United States Patent
Ferguson et al.

(10) Patent No.: US 7,008,402 B2
(45) Date of Patent: Mar. 7, 2006

(54) SAFETY SHIELD FOR MEDICAL NEEDLES

(75) Inventors: F. Mark Ferguson, Salt Lake City, UT (US); Charles V. Owen, Highland, UT (US); David L. Thorne, Kaysville, UT (US); Craig N. Thorne, Bountiful, UT (US); Mark Nelson, Sandy, UT (US); Gale H. Thorne, Jr., Bountiful, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 376 days.

(21) Appl. No.: 10/454,228

(22) Filed: Jun. 4, 2003

(65) Prior Publication Data

US 2003/0195475 A1    Oct. 16, 2003

Related U.S. Application Data

(62) Division of application No. 09/809,357, filed on Mar. 15, 2001, now Pat. No. 6,595,955.

(51) Int. Cl.
    *A61M 5/00*    (2006.01)
(52) U.S. Cl. ............. 604/110; 604/263; 604/162
(58) Field of Classification Search .......... 604/110, 604/263, 158, 162, 161, 264, 164.08
    See application file for complete search history.

(56) References Cited

U.S. PATENT DOCUMENTS

| 1,436,707 A | 11/1922 | Gaschke | |
|---|---|---|---|
| 4,332,323 A | 6/1982 | Reenstierna | 206/365 |
| 4,373,526 A | 2/1983 | Kling | 128/215 |
| 4,762,516 A | 8/1988 | Luther | 605/164 |
| 4,790,828 A | 12/1988 | Dombrowski | 604/198 |
| 4,804,371 A | 2/1989 | Vaillancourt | 604/198 |
| 4,826,490 A | 5/1989 | Byrne | 604/198 |
| 4,832,696 A | 5/1989 | Luther | 604/164 |
| 4,834,718 A | 5/1989 | McDonald | 604/195 |
| 4,846,811 A | 7/1989 | Vanderhoof | 604/263 |
| 4,917,669 A | 4/1990 | Bonaldo | 604/164 |
| 4,929,241 A | 5/1990 | Kulli | 604/263 |
| 4,931,048 A | 6/1990 | Lopez | 604/110 |
| 4,944,725 A | 7/1990 | McDonald | 604/164 |
| 4,950,252 A | 8/1990 | Luther | 604/198 |

(Continued)

FOREIGN PATENT DOCUMENTS

EP    0 702 972 B1    7/1995

(Continued)

*Primary Examiner*—Cris Rodriguez
(74) *Attorney, Agent, or Firm*—Paul S. Evans

(57) ABSTRACT

Medical needle shield apparatus for covering a needle after use. The medical needle shield apparatus is for use with a needle having proximal and distal ends, wherein the shield is slidably movable along the needle from a proximal position where the distal end of the needle is exposed, to a distal position where the shield covers the distal end of the needle. The shield comprises one or more clips having two or more apertures through which the needle passes, wherein the apertures have surfaces. A clip positioning member, in communication with at least one of the clips, positions the aperture surfaces of at least one of the clips when a portion of the clip positioning member in contact with the needle is advanced past the distal end of the needle such that at least a portion of the aperture surfaces of the two or more apertures binds to the needle with opposing binding forces so as to secure the shield to the needle.

20 Claims, 45 Drawing Sheets

U.S. PATENT DOCUMENTS

| | | | |
|---|---|---|---|
| 4,952,207 A | 8/1990 | Lemieux | 604/164 |
| 4,964,854 A | 10/1990 | Luther | 604/166 |
| 4,978,344 A | 12/1990 | Dombrowski | 604/198 |
| 4,994,041 A | 2/1991 | Dombrowski | 604/164 |
| 5,007,901 A | 4/1991 | Shields | 604/110 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,059,180 A | 10/1991 | McLees | 604/110 |
| 5,084,023 A | 1/1992 | Lemieux | 604/167 |
| 5,084,030 A | 1/1992 | Byrne | 604/198 |
| 5,085,648 A | 2/1992 | Purdy | 604/198 |
| 5,127,905 A | 7/1992 | Lemieux | 604/164 |
| 5,135,504 A | 8/1992 | McLees | 604/164 |
| 5,147,327 A | 9/1992 | Johnson | 604/198 |
| 5,171,229 A | 12/1992 | McNeil | 604/192 |
| 5,183,468 A | 2/1993 | McLees | 604/164 |
| 5,205,829 A | 4/1993 | Lituchy | 604/164 |
| 5,215,528 A | 6/1993 | Purdy | 604/164 |
| 5,279,591 A * | 1/1994 | Simon | 604/263 |
| 5,300,045 A | 4/1994 | Plassche | 604/263 |
| 5,312,371 A | 5/1994 | Dombrowski | 604/198 |
| 5,322,517 A | 6/1994 | Sircom | 604/198 |
| 5,328,482 A | 7/1994 | Sircom | 604/164 |
| 5,334,158 A | 8/1994 | McLees | 604/110 |
| 5,342,310 A | 8/1994 | Ueyama | 604/164 |
| 5,344,408 A | 9/1994 | Partika | 604/192 |
| 5,348,544 A | 9/1994 | Sweeney | 604/192 |
| 5,411,486 A | 5/1995 | Zadini | 604/198 |
| 5,417,659 A | 5/1995 | Gaba | 604/110 |
| 5,419,766 A | 5/1995 | Chang | 604/110 |
| 5,423,766 A | 6/1995 | Di Cesare | 604/192 |
| 5,458,658 A | 10/1995 | Sircom | 604/192 |
| 5,478,313 A | 12/1995 | White | 604/110 |
| 5,487,733 A | 1/1996 | Caizza et al. | 604/110 |
| 5,531,704 A | 7/1996 | Knotek | 604/192 |
| 5,533,974 A | 7/1996 | Gaba | 604/110 |
| 5,538,508 A | 7/1996 | Steyn | 604/192 |
| 5,549,570 A | 8/1996 | Rogalsky | 604/198 |
| 5,558,651 A | 9/1996 | Crawford | 604/192 |
| 5,562,624 A | 10/1996 | Righi | 604/110 |
| 5,562,633 A * | 10/1996 | Wozencroft | 604/171 |
| 5,582,597 A | 12/1996 | Brimhall et al. | 604/192 |
| 5,584,809 A | 12/1996 | Gaba | 604/110 |
| 5,584,810 A | 12/1996 | Brimhall | 604/110 |
| 5,584,818 A | 12/1996 | Morrison | 604/197 |
| 5,599,310 A | 2/1997 | Bogert | 604/164 |
| 5,601,532 A | 2/1997 | Gaba | 604/110 |
| 5,601,536 A | 2/1997 | Crawford | 604/263 |
| 5,611,781 A | 3/1997 | Sircom | 604/164 |
| 5,662,610 A | 9/1997 | Sircom | 604/110 |
| 5,683,365 A | 11/1997 | Brown | 604/110 |
| 5,697,907 A | 12/1997 | Gaba | 604/110 |
| 5,718,688 A | 2/1998 | Wozencroft | 604/164 |
| 5,725,504 A | 3/1998 | Collins | 604/165 |
| 5,749,856 A | 5/1998 | Zadini | 604/162 |
| 5,853,393 A | 12/1998 | Bogert | 604/165 |
| 5,879,337 A | 3/1999 | Kuracina | 604/192 |
| 5,882,337 A | 3/1999 | Bogert | 604/110 |
| 5,910,130 A | 6/1999 | Caizza et al. | 604/110 |
| 5,911,705 A | 6/1999 | Howell | 604/110 |
| 5,951,515 A | 9/1999 | Osterlind | 604/110 |
| 5,980,488 A | 11/1999 | Thorne | 604/110 |
| 6,001,080 A | 12/1999 | Kuracina | 604/171 |
| 6,004,294 A | 12/1999 | Brimhall | 604/164 |
| 6,117,108 A | 9/2000 | Woehr | 604/110 |
| 6,132,401 A | 10/2000 | Van Der Meyden | 604/195 |
| 6,193,694 B1 | 2/2001 | Bell | 604/192 |
| 6,203,527 B1 | 3/2001 | Zadini | 604/110 |
| 6,210,373 B1 | 4/2001 | Allmon | 604/192 |
| 6,221,047 B1 | 4/2001 | Green et al. | 604/164 |
| 6,280,419 B1 | 8/2001 | Vojtasek | 604/192 |
| 6,287,278 B1 | 9/2001 | Woehr et al. | 604/110 |
| 6,406,459 B1 | 6/2002 | Allmon | 604/192 |
| 6,443,927 B1 | 9/2002 | Cook | 604/110 |
| 6,443,929 B1 | 9/2002 | Kuracina et al. | 604/192 |
| 6,585,704 B1 | 7/2003 | Luther et al. | 604/263 |
| 6,616,630 B1 | 9/2003 | Woehr et al. | 604/110 |
| 6,623,458 B1 | 9/2003 | Woehr et al. | 604/192 |
| 6,629,959 B1 | 10/2003 | Kuracina et al. | 604/192 |
| 6,652,486 B1 * | 11/2003 | Bialecki et al. | 604/110 |
| 6,682,510 B1 | 1/2004 | Niermann | 604/263 |
| 2002/0099339 A1 | 7/2002 | Niermann | 604/263 |
| 2002/0107483 A1 | 8/2002 | Cook | 604/164.01 |
| 2002/0177813 A1 | 11/2002 | Adams et al. | 604/164.07 |
| 2002/0177818 A1 | 11/2002 | Vaillancourt | 604/198 |
| 2003/0036731 A1 | 2/2003 | Wilkinson et al. | 604/198 |
| 2003/0114797 A1 | 6/2003 | Vaillancourt et al. | 604/171 |
| 2003/0135157 A1 | 7/2003 | Saulenas et al. | 604/110 |
| 2003/0144627 A1 | 7/2003 | Woehr et al. | 604/110 |
| 2003/0195471 A1 | 10/2003 | Woehr et al. | 604/164.08 |
| 2003/0195479 A1 | 10/2003 | Kuracina et al. | 604/263 |
| 2003/0216687 A1 | 11/2003 | Hwang | 604/110 |
| 2004/0010227 A1 | 1/2004 | Riesenberger et al. | 604/110 |
| 2004/0049155 A1 | 3/2004 | Schramm | 604/110 |

FOREIGN PATENT DOCUMENTS

| | | |
|---|---|---|
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 6/2002 |
| WO | WO 03/103757 A1 | 12/2003 |

* cited by examiner

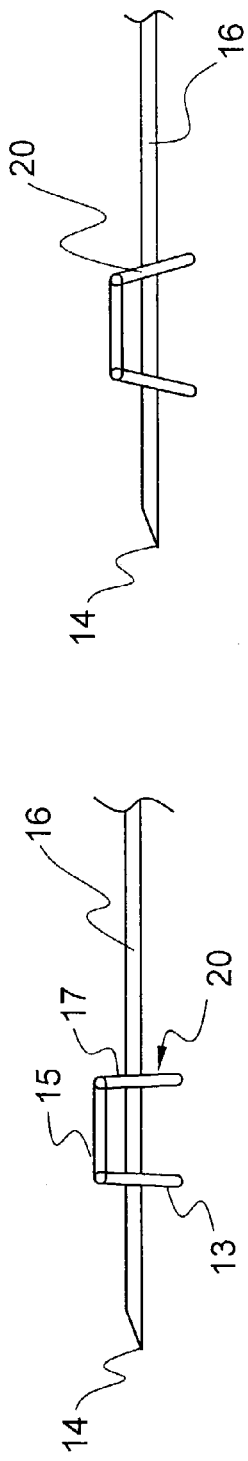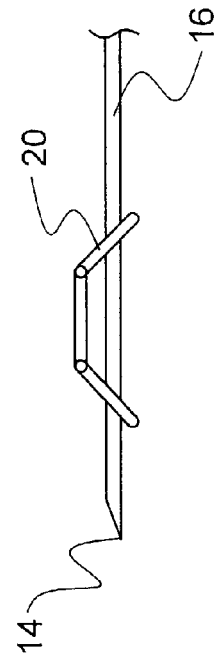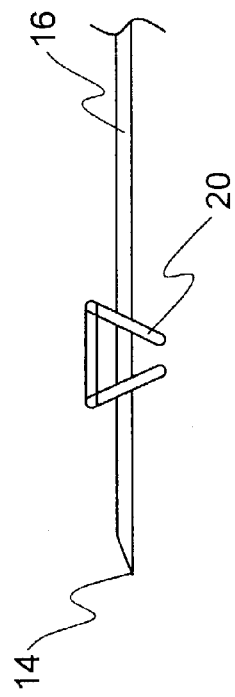
FIGURE 7A  FIGURE 7C  FIGURE 7B  FIGURE 7D

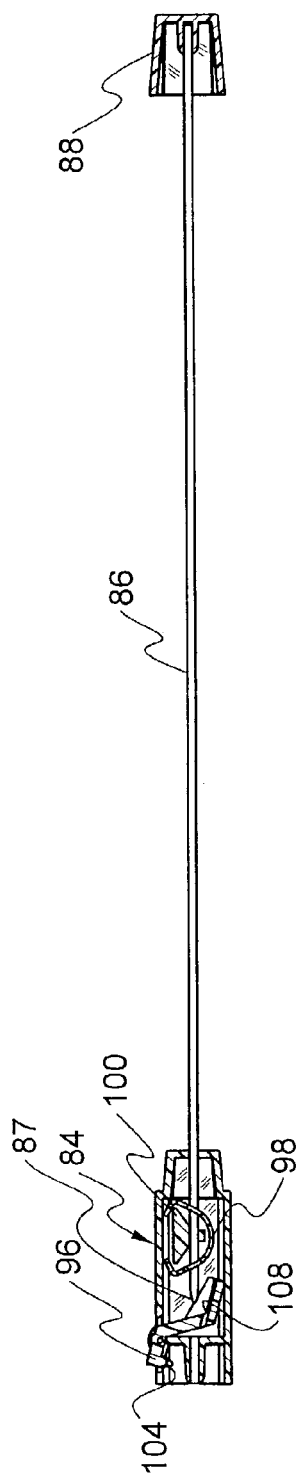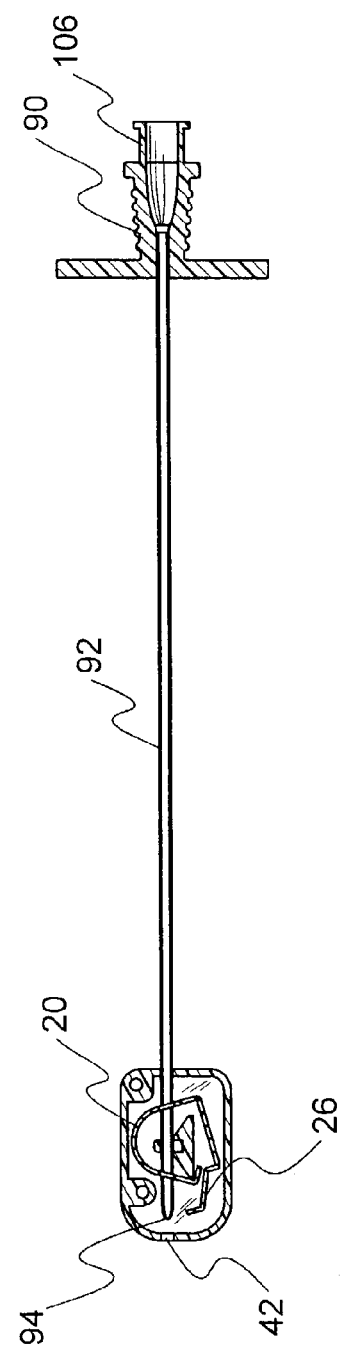

SAFETY SHIELD FOR MEDICAL NEEDLES

This application is a Divisional of application Ser. No. 09/809,357 filed in the United States Patent & Trademark Office on Mar. 15, 2001 now U.S. Pat. No. 6,595,955.

FIELD OF THE INVENTION

This invention relates to safety shields for medical needles, and more particularly to safety shields that are axially movable along a needle cannula from a proximal position where the tip of the needle is exposed to a distal position where the tip of the needle is covered.

BACKGROUND OF THE INVENTION

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne diseases.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical medical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Current devices for protecting medical needles often require two hands, and with some devices the safety status of needle protection is not readily apparent. Other problems of current safety devices include difficulty of use and high cost due to their complexity and number of parts.

There remains a need to provide a more satisfactory solution to a needle safety device.

SUMMARY OF THE INVENTION

The present invention was developed to fill a need for a device which effectively and inexpensively protects a medical needle after use.

The present invention seeks to resolve a number of the problems which have been experienced in the background art, as identified above. More specifically, the apparatus and method of this invention constitute an important advance in the art of safety needle devices, as evidenced by the following objects and advantages realized by the invention over the background art.

An object of the present invention is to provide a safety needle device which is intuitive and easy to use.

Another object of the invention is to provide a safety device with a minimum number of parts.

Yet another object of the present invention is to provide a safety needle device which is deployed by finger actuation, or in some embodiments by passive actuation.

A further object of the present invention is to be either integral with a medical needle device or attachable as a separate part.

Additional objects and advantages of the invention will be apparent from the description which follows, or may be learned by the practice of the invention.

Briefly summarized, the foregoing objects are achieved by a medical needle shield apparatus for use with a needle having proximal and distal ends, comprising a shield slidably movable along the needle from a proximal position where the distal end of the needle is exposed, to a distal position where the shield covers the distal end of the needle. The shield comprises: one or more clips having a total of two or more apertures through which the needle passes, and the apertures have surfaces which contact the needle; and a clip positioning member in communication with at least one of the clips for positioning the aperture surfaces of at least one of the clips when a portion of the clip positioning member in contact with the needle is advanced past the distal end of the needle such that at least a portion of the aperture surfaces of the two or more apertures binds to the needle with opposing binding forces so as to secure the shield to the needle.

BRIEF DESCRIPTION OF THE DRAWINGS

FIGS. 7A–7D illustrate various embodiments of the clip.

FIG. 29 is a lateral cross sectional view of the medical needle shield apparatus of FIG. 28.

FIG. 31 is a lateral cross sectional view of the medical needle shield apparatus of FIG. 30.

DETAILED DESCRIPTION OF THE INVENTION

In this description, the term proximal is generally used to indicate relative nearness of a referenced item to a user of a device or a viewer of a perspective drawing of a figure. The term distal is similarly used to indicate relative remoteness. Reference is now made to the embodiments illustrated in FIGS. 1–41 wherein like numerals are used to designate like parts throughout. In cases where parts have similar, but not identical, form and function, numerals with primes may be used for ease in interpretative cross-referencing.

Figure 1:
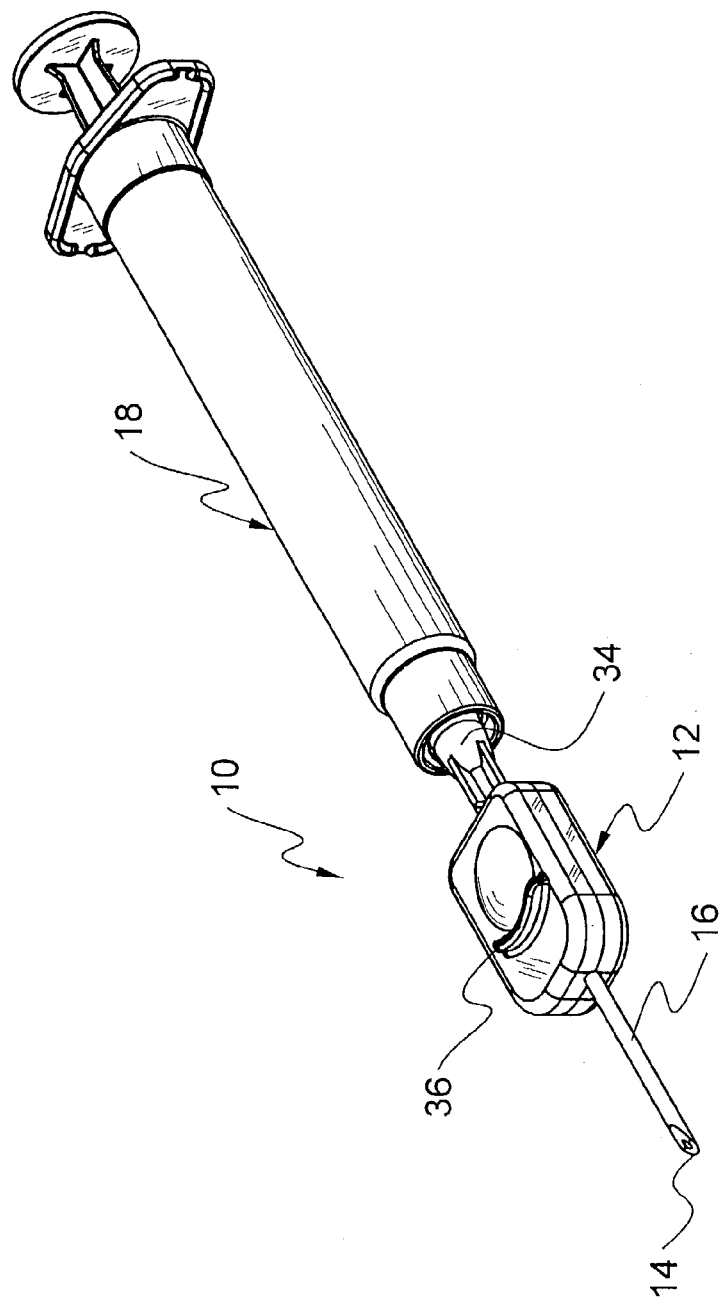
FIG. 1 is a perspective view of a medical needle shield apparatus having a shield slidably movable along a needle in a pre-use condition.

FIG. 1 provides an overview of the salient operating features of an embodiment of a medical needle safety shield assembly 10 for use with a needle 16 having proximal distal ends. FIGS. 1–6 illustrate the needle 16 being connected to a luer fitting 34. As shown in FIGS. 1–6, the shield assembly 10 comprises a shield 12 slidably movable along the needle 16 from a proximal position where the distal end 14 of the needle 16 is exposed, to a distal position where the shield 12 covers the distal end 14 of the needle 16. The shield 12 comprises one or more clips 20 having two or more apertures 22 through which the needle 16 passes. The apertures 22 have surfaces 24 which contact the needle 16. A clip positioning member 26 is in communication with at least one of the clips 20 for positioning the aperture surface 24 of at least one of the clips 20 when a portion 38 of the clip positioning member 26 in contact with the needle 16 is advanced past the distal end 14 of the needle 16, such that at least a portion of the aperture surfaces 24 of the two or more apertures 22 binds to the needle 16 with opposing binding forces so as to secure the shield 12 to the needle 16. FIGS. 1–6 illustrate clip 20 being integrally connected with the clip positioning member 26, wherein the clip is held in a biased state by a retention surface 28 disposed on the clip positioning member 26. The clip positioning member 26 may cause movement of the one or more clips 20 or allow movement of the one or more clips 20. FIGS. 1–6 illustrate the shield 12 further comprising a housing having an upper portion 30 and a lower portion 32 for encapsulating the shield 12. The housing may be integral with the clip 20 and clip positioning member 26.

The clip 20 design shown has a self-energizing characteristic such that as a force is increasingly applied to the needle 16 in either direction along the axis of the needle 16, the clip 20 more securely attaches itself to the needle 16. Reference to opposing binding forces generated by the one or more clips 20 on the needle 16 means the forces generated between the one or more clips 20 and the needle 16 which oppose proximal and distal forces. In other words, one aperture surface 24 of the one or more clips 20 creates a binding force in one direction, while the other aperture surface 24 creates a binding force in the opposite direction. This is due to the aperture surfaces 24 being rotated in opposite directions upon actuation.

Figure 2:
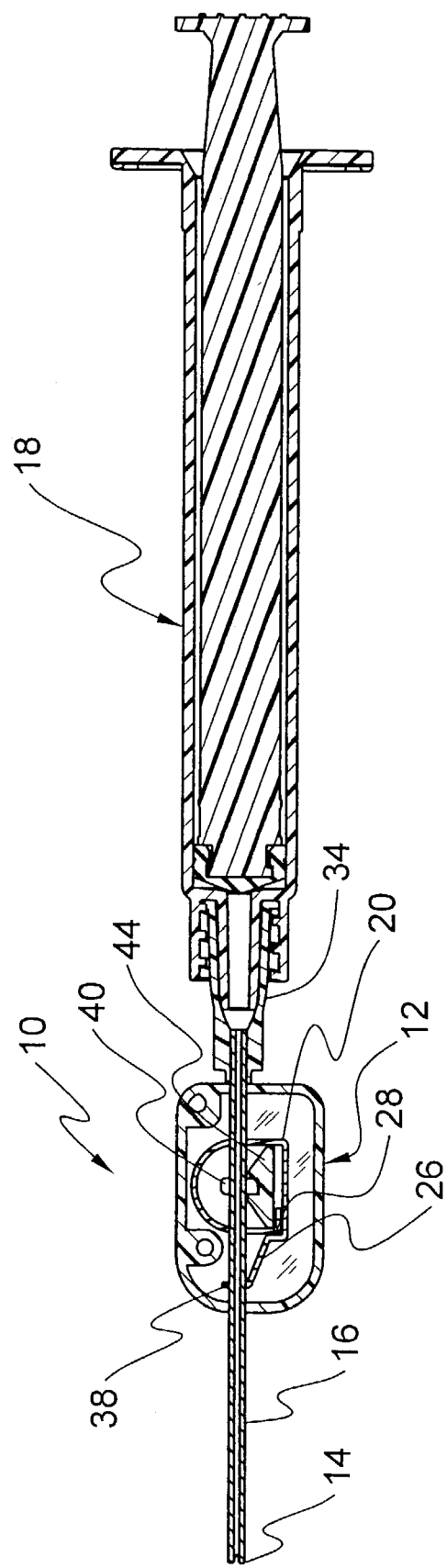
FIG. 2 is a lateral cross sectional view of the medical needle shield apparatus of FIG. 1.
Figure 3A:
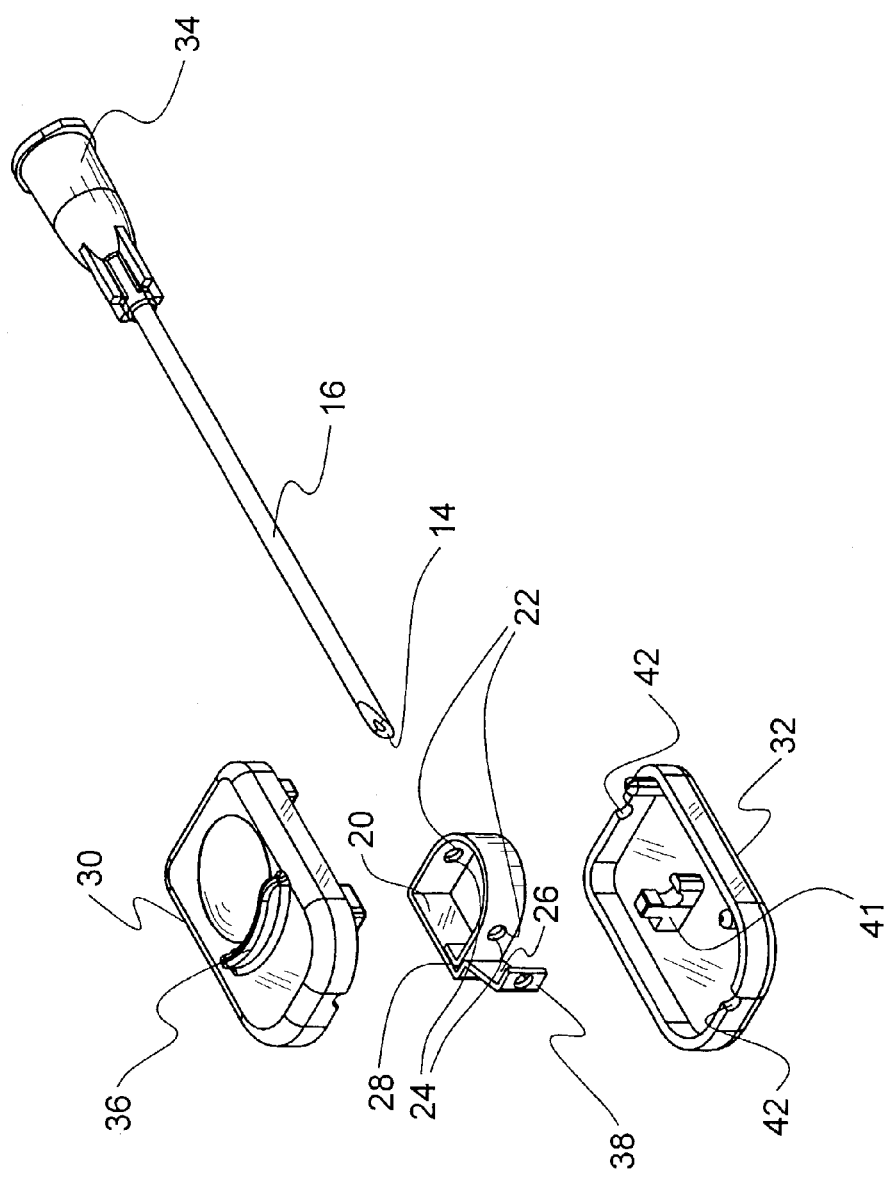
FIG. 3A is a perspective view of the components of the medical needle shield apparatus of FIG. 1.
Figure 3B:
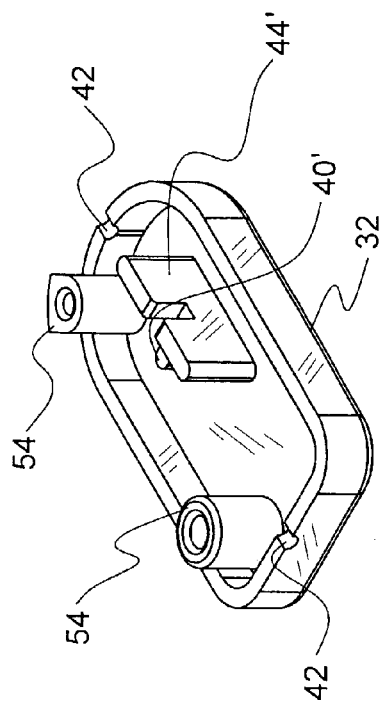
FIG. 3B is a perspective view of the lower housing shown in FIG. 3A.
Figure 3D:
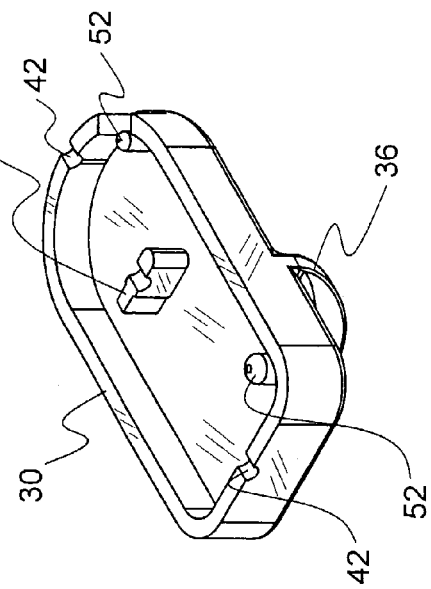
FIG. 3D is a perspective view of the underside of upper housing shown in FIG. 3A.
Figure 3C:
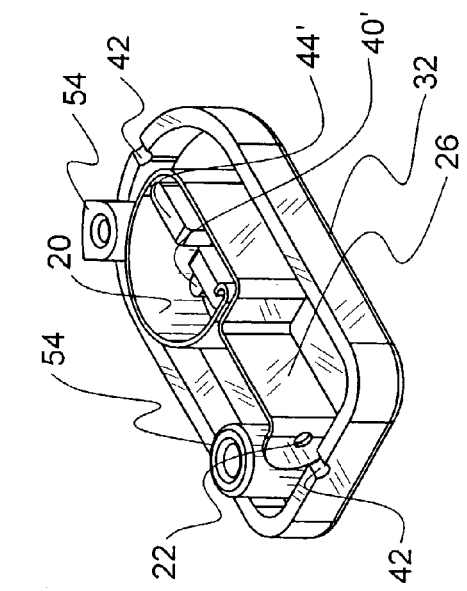
FIG. 3C is a perspective view of the lower housing and clip shown in FIG. 3A.
Figure 4:
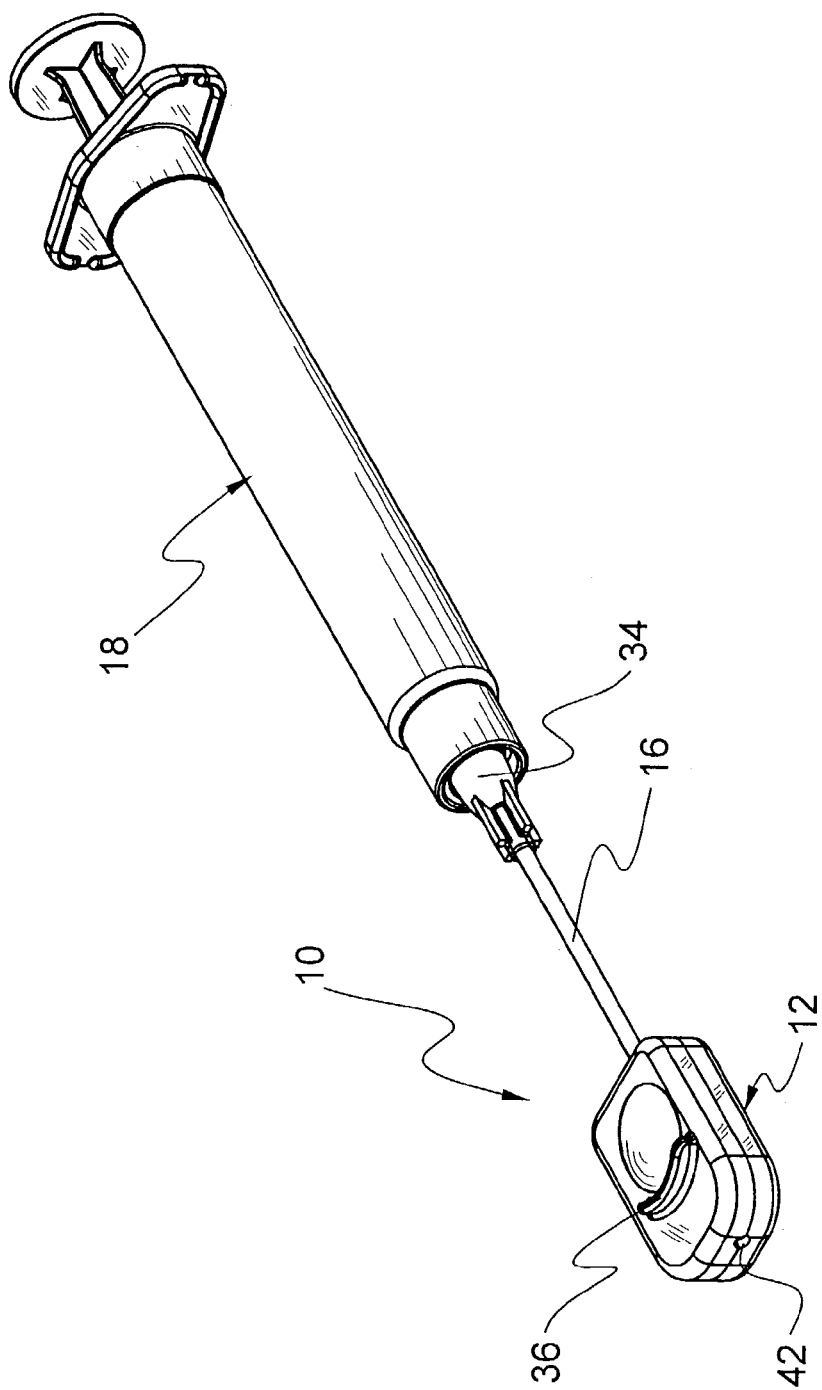
FIG. 4 is a perspective view of the medical needle shield apparatus of FIG. 1 in a post-use, shielded position.
Figure 5:
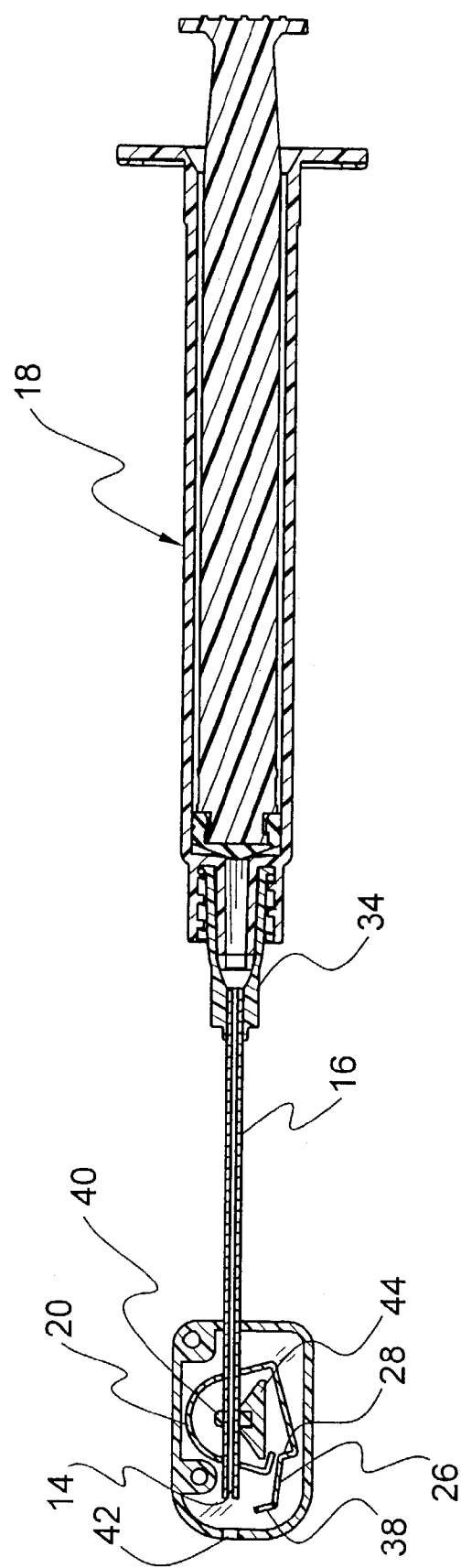
FIG. 5 is a lateral cross sectional view of the medical needle shield apparatus of FIG. 4.
Figure 6:
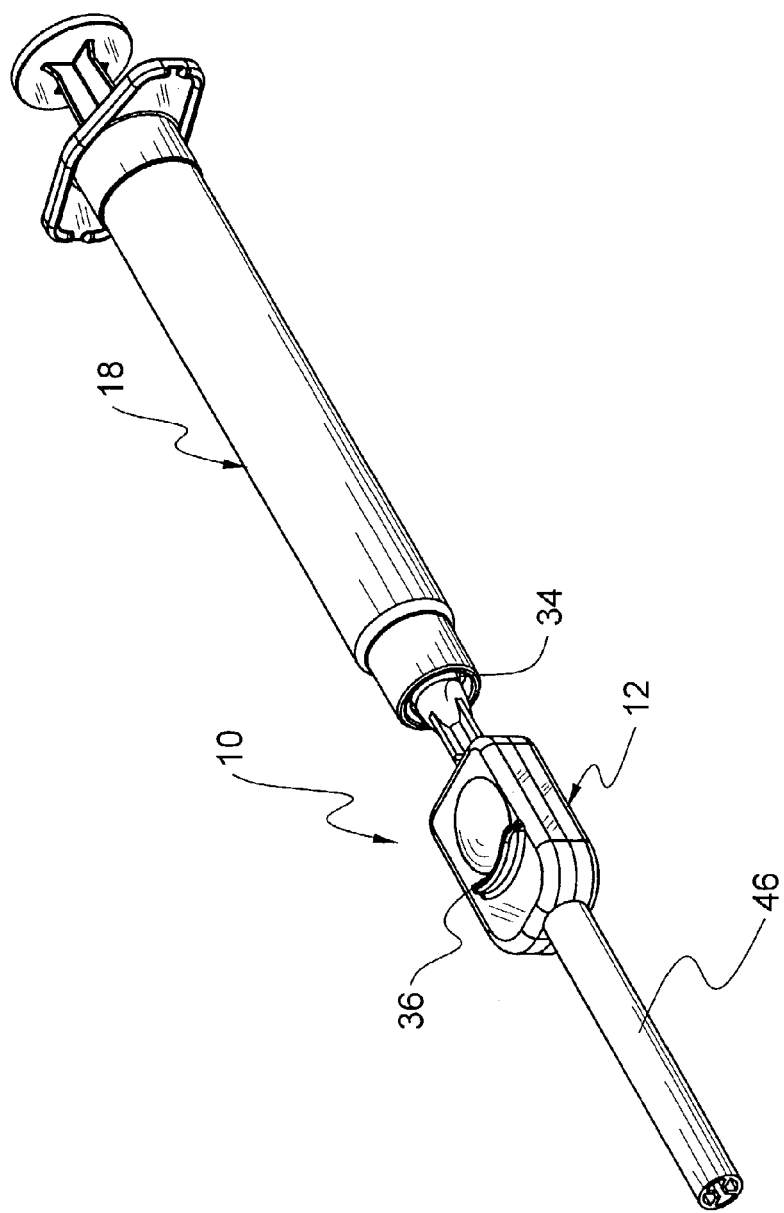
FIG. 6 is a perspective view of the medical needle shield apparatus of FIG. 1 with a needle cover placed over the needle prior to use.

FIGS. 1, 2 and 6 show the safety shield assembly 10 in a pre-use state, while FIGS. 4 and 5 show the post-use and protected state.

FIGS. 1–6 illustrate a safety shield assembly 10 for a syringe 18; however, the safety shield 10 may be utilized with essentially all medical needle applications including, but not limited to, phlebotomy devices, catheters, catheter introducers, guide wire introducers, spinal and epidural, biopsy, apheresis, dialysis, blood donor, Verus needles, Huber needles and so forth.

Various clip and biasing options are available for the clip 20 design. The following examples shown herein are intended to be illustrative, but not limited, to those embodiments shown. The clip 20 may also comprise multiple elements pivotally connected as shown in FIGS. 7A–7D, 8A–8G, 9A–9L, 10A–10B, and 11C–11D. The clip 20 may also comprise one or more clips. For example, the clip 20 illustrated in FIG. 7A may be embodied in another design wherein a first clip 13 and a second clip 17 are not connected by element 15. For this embodiment, the clip positioning member 26 may be designed such that it properly positions both the first clip 13 and second clip 17 for binding to the needle 16 when it is actuated upon sensing the distal end 14 of the needle 16. Alternatively, the elements of the clip 20 may be continuous. The function is to provide for a clip 20 which binds to the needle 16 on at least two points when properly positioned by the clip positioning member 26. The clip 20 may be either biased or unbiased. If the clip 20 is unbiased, the clip positioning member 26 will need to provide a sufficient force on the clip 20 when a portion 38 of the clip positioning member 26 is advanced past the distal end 14 of the needle 16 to ensure that aperture surfaces 24 bind to the needle 16. The apertures 22 in the clip 20 are not limited to circular shapes. Other shapes include, but are not limited to, diamond-shaped (provides for wedge action with amplification of binding force), a slot or a forked opening. The purpose of the apertures 22 is to create a dual lockout that will prevent movement of the clip 20 along the needle 16 in both directions due to opposing binding forces at two points of intersection between the clip 20 and needle 16. FIG. 7A illustrates a clip 20 in an initial position, wherein the shield 12 (not shown) is free to slide along needle 16. FIG. 7B illustrates the clip 20 in the binding position wherein the clip 20 binds to the needle 16 and secures the shield 12. FIG. 7C illustrates a clip 20 in an initial position, wherein the shield 12 (not shown) is free to slide along needle 16. FIG. 7D illustrates the clip in the binding position, wherein the clip 20 binds to the needle 16 and secures the shield 12.

Figure 8A:
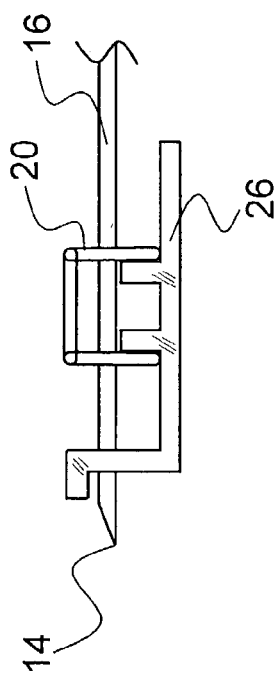
FIGS. 8A–8G illustrate various clip and clip positioning member embodiments.
Figure 8C:
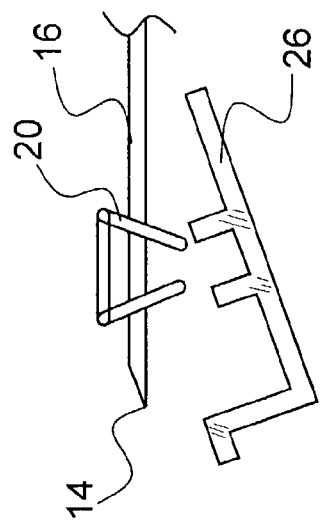
Figure 8B:
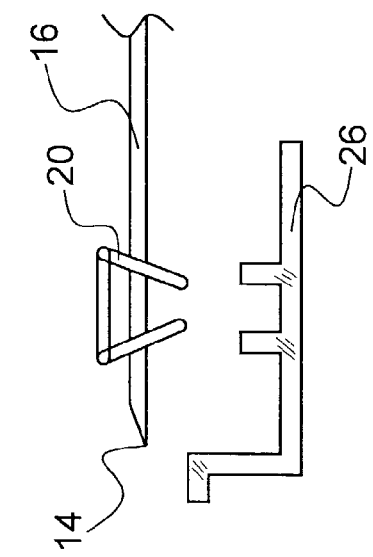
Figure 8D:
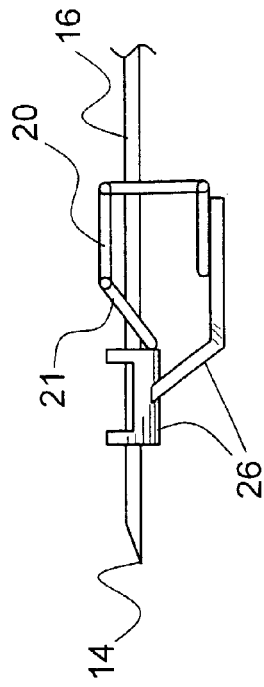
Figure 8F:
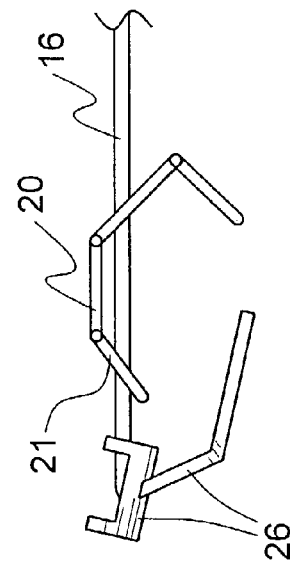
Figure 8E:
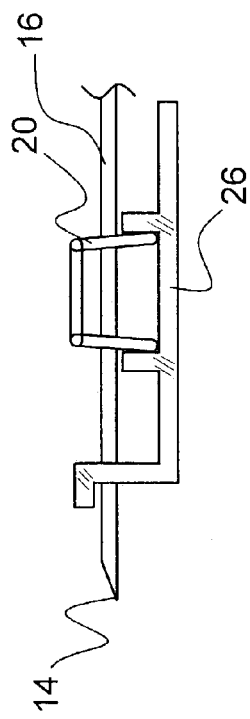

FIG. 8A illustrates one embodiment of a clip 20 biased inward, which is free to slide along the needle 16 before the clip positioning member 26 senses the distal end 14 of a needle 16. FIG. 8B shows the clip positioning member 26, as shown in FIG. 8A, releasing the biased clip 20 after the clip positioning member 26 senses the distal end 14 of a needle 16. FIG. 8B shows the clip positioning member 26 moving downward as it senses the distal end 14 of a needle 16. FIG. 8C shows the clip positioning member 26 rotating as it senses the distal end 14 of a needle 16. FIG. 8D illustrates another embodiment of a clip 20 biased outward, which is free to slide along the needle 16 before the clip positioning member 26 senses the distal end 14 of a needle 16. FIG. 8E shows the clip positioning member 26, as shown in FIG. 8D, releasing the biased clip 20 after the clip positioning member 26 senses the distal end 14 of a needle 16.

Figure 8G:
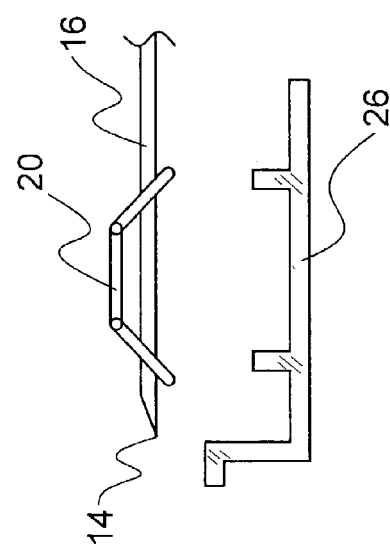
Figure 9C:
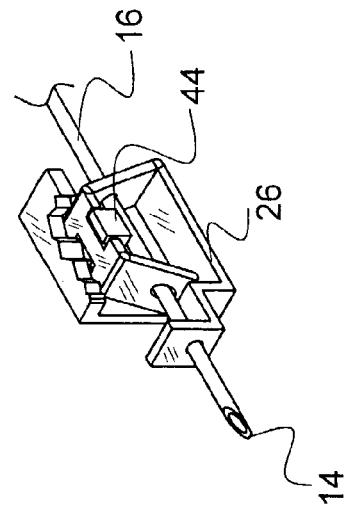
FIGS. 9A–9L illustrate the interplay between various clip, clip positioning member and clip support embodiments.
Figure 9D:
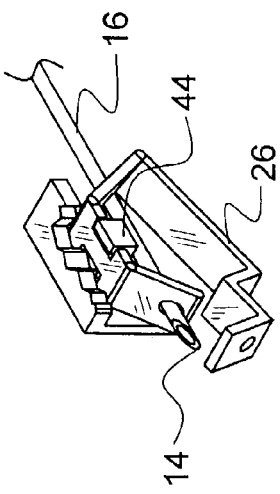
Figure 9A:
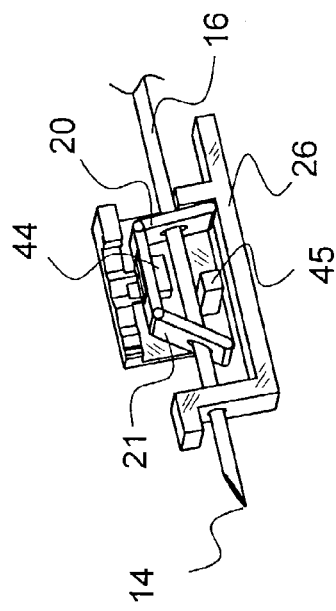
Figure 9B:
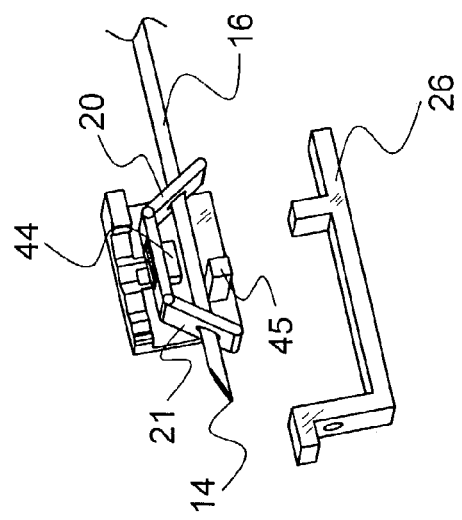
Figure 9E:
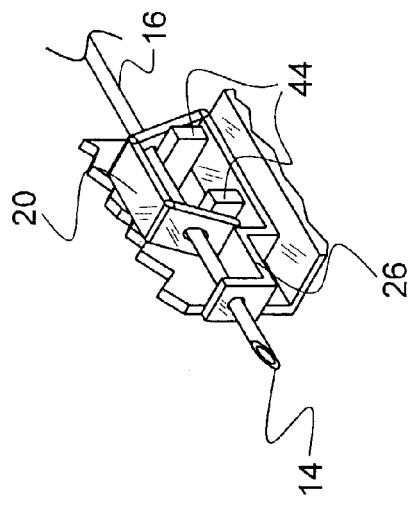
Figure 9G:
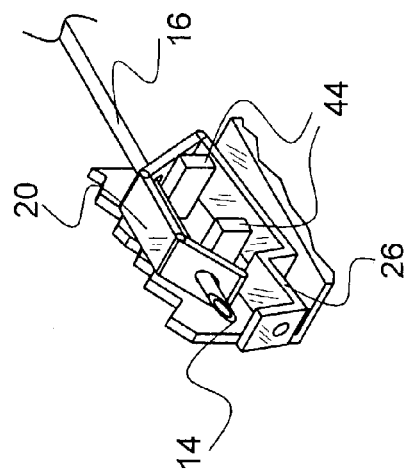
Figure 9F:
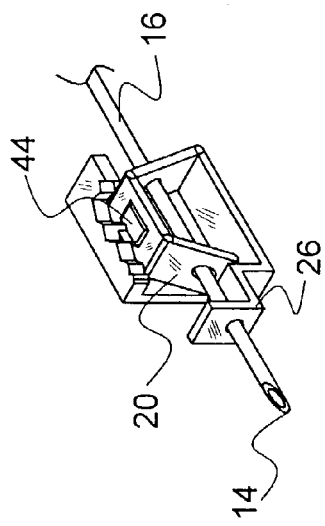
Figure 9H:
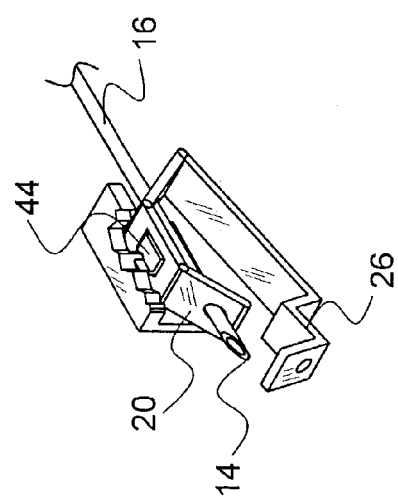
Figure 9I:
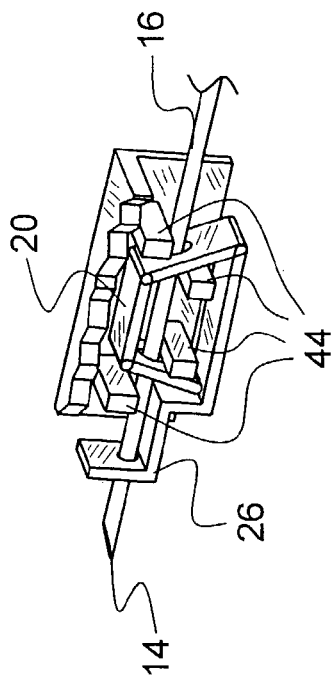
Figure 9K:
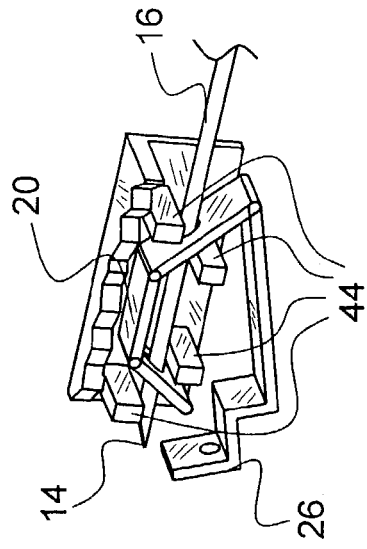
Figure 9J:
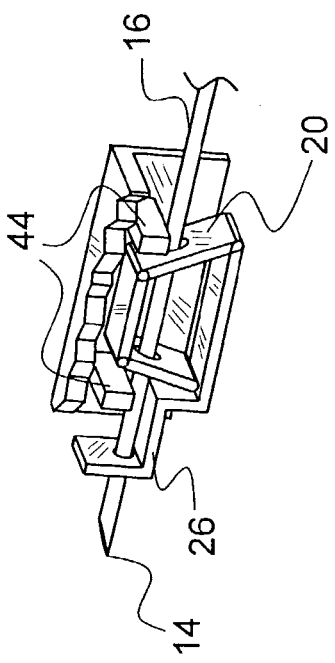
Figure 9L:
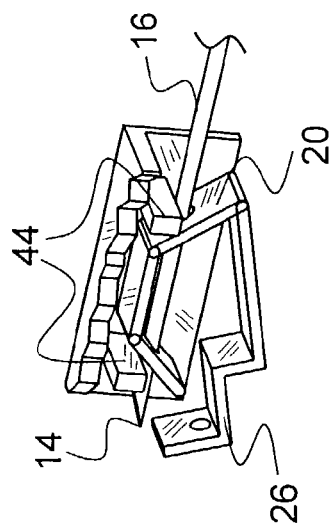

One of the clips 20 may be a one-way clutch 21 continually binding on the needle 16 and allowing for movement in only one direction (e.g., towards the distal end 14 of the needle 16). FIG. 8F shows a one-way clutch 21 and clip 20 which are free to slide along the needle 16 before the clip positioning member 26 senses the distal end 14 of a needle 16. FIG. 8G shows the clip positioning member 26, as shown in FIG. 8F, releasing the biased clip 20 after the clip positioning member 26 senses the distal end 14 of a needle 16. FIGS. 9A–9L illustrate various interplay between the clip 20, the clip positioning member 26 and the clip support 44. FIG. 9A shows a one-way clutch 21 and clip 20 supported by clip supports 44 and 45, which are free to slide along the needle 16 before the clip positioning member 26 senses the distal end 14 of a needle 16. The function of clip support 44 is to provide binding forces on the clip 20 or to preclude forces on the clip 20 that diminish binding forces. Clip support 45 prevents clip 20 from toggling backwards and binding prematurely. FIG. 9B shows the clip positioning member 26, as shown in FIG. 9A, releasing the biased clip 20 after the clip positioning member 26 senses the distal end 14 of a needle 16. FIGS. 9C–9L illustrate various other embodiments showing the pre-activation and secure positions of the clip 20 on the needle 16 with various clip support 44 configurations. For example, FIGS. 9E and 9F show a clip support 44 resting in a slot located in the clip 20 for holding the clip 20 in place before (FIG. 9E) and after actuation (FIG. 9F). Clip supports 44 shown in FIGS. 9G and 9H place forces into the underside of clip 20 to cause it to expand upon activation. Clip supports 44 shown in FIGS. 9I and 9J place forces into the top of the clip 20 to cause it to expand upon activation.

Figure 10A:
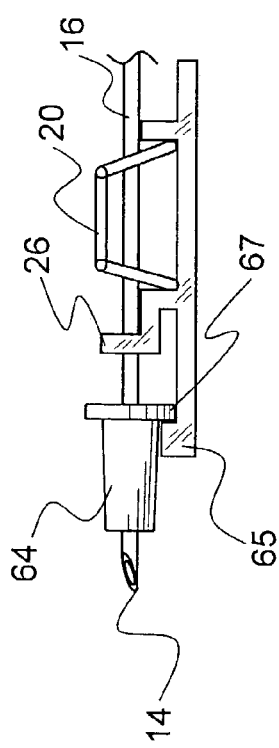
FIGS. 10A–10B illustrate one embodiment of the clip and clip positioning member for a catheter.
Figure 10B:
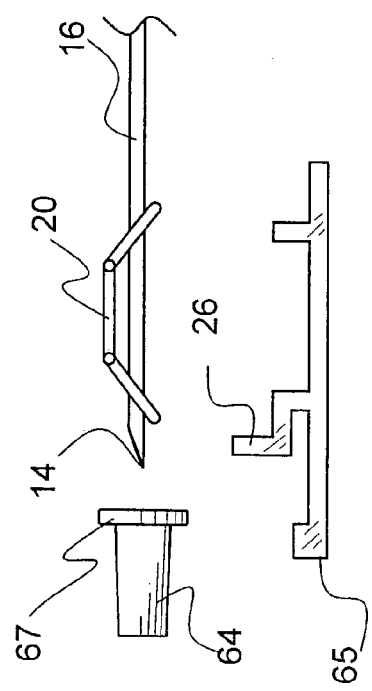

FIG. 10A illustrates a catheter embodiment of the present invention where a clip 20 is biased outward and is free to slide along the needle 16 before the clip positioning member 26 senses the distal end 14 of a needle 16. A retainer 65 in communication with the clip positioning member 26 retains a catheter hub 64 along a flanged surface 67. Alternatively, the catheter hub 64 and retainer 65 may comprise cooperating detents and detent pockets for mutually engaging to hold the catheter hub 64 to the shield. FIG. 10B shows the clip positioning member 26 and retainer 65, as shown in FIG. 10A, releasing the biased clip 20 and catheter hub 64 after the clip positioning member 26 senses the distal end 14 of a needle 16.

Figure 11C:
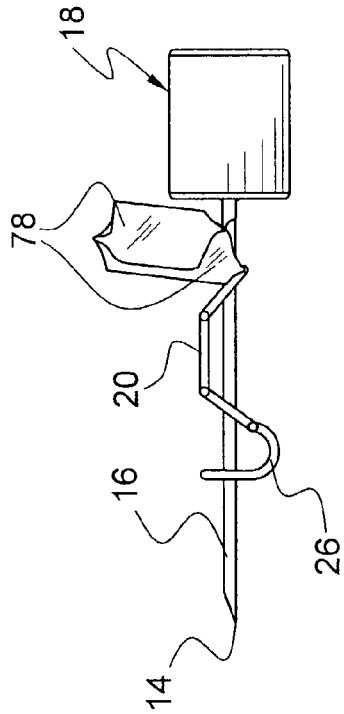
FIGS. 11A–11H illustrate various methods to provide shield advancement.
Figure 11D:
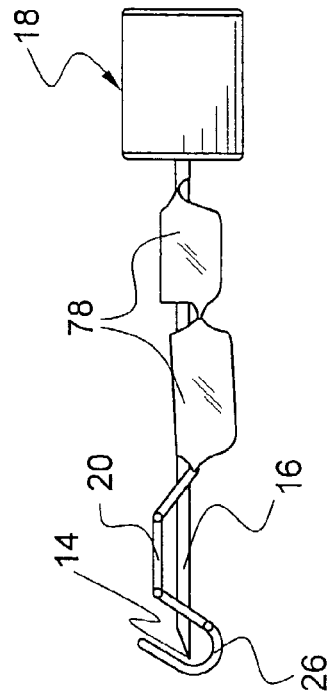
Figure 11A:
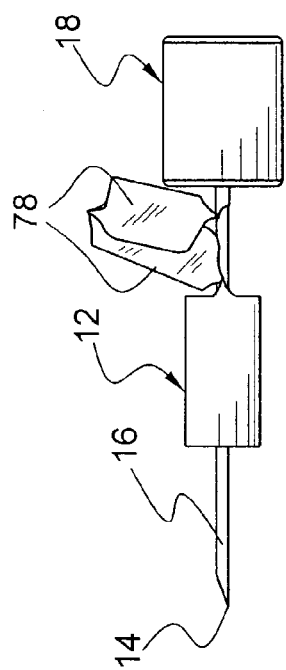
Figure 11B:
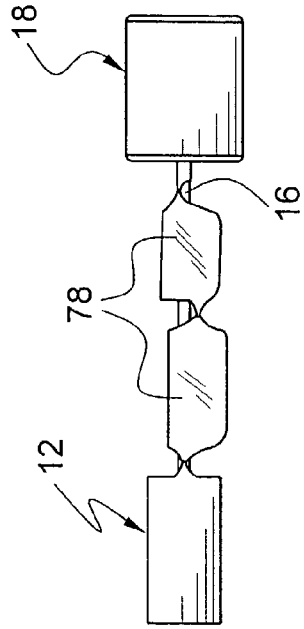

FIGS. 11A–11H illustrate various embodiments of the present invention, wherein the shield 12 is attached to the hub of a medical needle device, such as a syringe 18. For example, as shown in FIGS. 11A–11D the safety shield assembly 10 may comprise two or more segments 78 hingedly connected to each other and articulated to the shield 12. The two or more segments 78 are movable from a folded condition where the shield 12 is in a proximal position and the distal end 14 of the needle 16 is exposed, to an extended position where the shield 12 extends beyond the distal end 14 of the needle 16. FIGS. 11C and 11D show another possible configuration for the clip 20 and clip positioning member 26 connected to two or more segments 78. FIGS. 11C and 11D are a specific design wherein the force applied to the clip 20 by the two or more segments 78 unlocks the clip 20 and allows it to move distally. The clip 20 may or may not have a housing enclosing the clip 20.

Figure 11G:
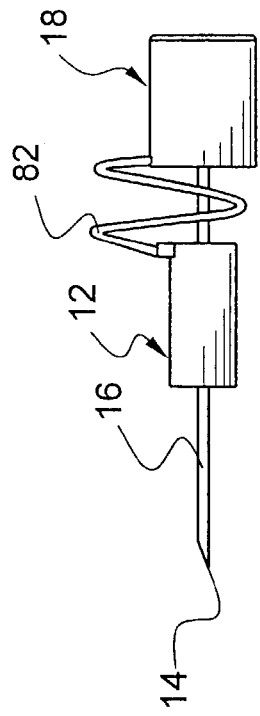
Figure 11H:
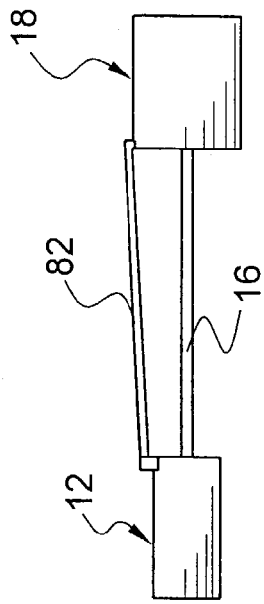
Figure 11E:
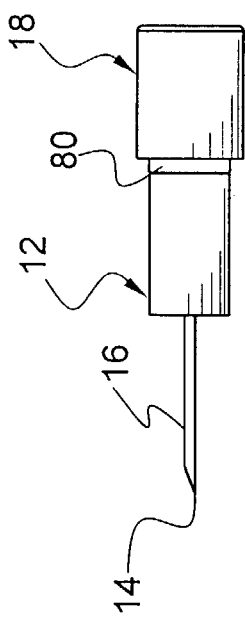
Figure 11F:
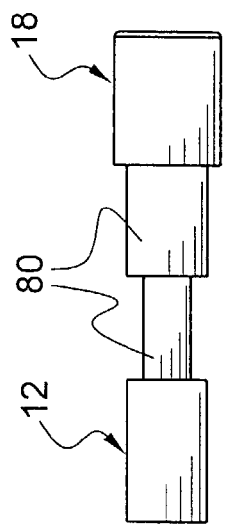

Another example of attaching the shield 12 to a medical needle device is by means of two or more telescoping members 80 as shown in FIGS. 11E and 11F. Yet another example of attaching the shield 12 to a medical needle device is by means of a flexible and resilient tether 82 as shown in FIGS. 11G and 11H.

Health care workers will detect the locking of the safety shield assembly 10 to the needle 16 when axial movement of the shield assembly 10 is impeded by the activation of the clip positioning member 26, which causes the clip 20 to bind to the needle 16. An audible clicking sound typically occurs when the clip positioning member 26 causes the clip 20 to bind to the needle 16, thereby further alerting the health care worker that the safety shield assembly 10 is in the locked position over the distal end 14 of the needle 16.

The housing which encapsulates the clip 20 and clip positioning member 26 can be embodied in many optional configurations for protectively enclosing distal end 14 of the needle 16. Various examples are shown in FIGS. 3A–3D, wherein the housing comprises an upper portion 30 and a lower portion 32. A tab 36 may be disposed on the housing for assisting in moving the shield 12 axially along the needle 16 as a health care worker presses against the tab 36 with a finger. The shield 12 may also be moved to the distal position by pressing against a surface which catches the shield 12. The housing may further comprise lower and upper needle supports 40 (40') and 41 (41') respectively, and openings 42 in the end walls of the housing for supporting the needle 16 as the shield is moved axially. The housing may also comprise clip support 44 (44') for ensuring the proper positioning of the clip 20 before and after actuation. As shown, the clip support 44 (44') enhances the binding force of the clip 20 on the needle 16 after actuation. Care should be given to the placement and geometry of clip support 44 (44') so as to not diminish the binding force of clip 20 on needle 16. Cooperating detents 52 and detent pockets 54 aid in the attachment of the upper portion 30 to the lower portion 32 of the housing.

As shown in FIG. 6, a needle cover 46 is commonly used to protect needles 16 prior to use and to prevent inadvertent actuation of the safety shield assembly 10 before cover 46 is removed for use of needle 16.

Figure 12:
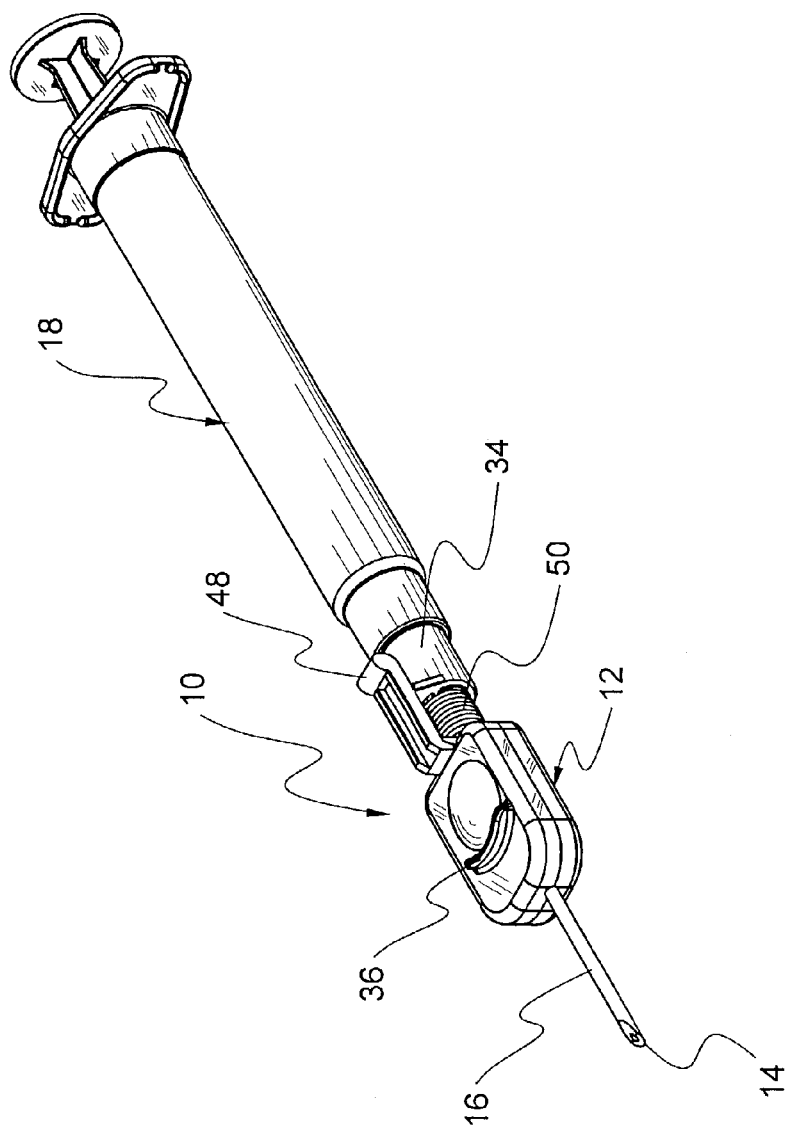
FIG. 12 is a perspective view of the medical needle shield apparatus of FIG. 1 with a spring-loaded shield to provide shield advancement.
Figure 13:
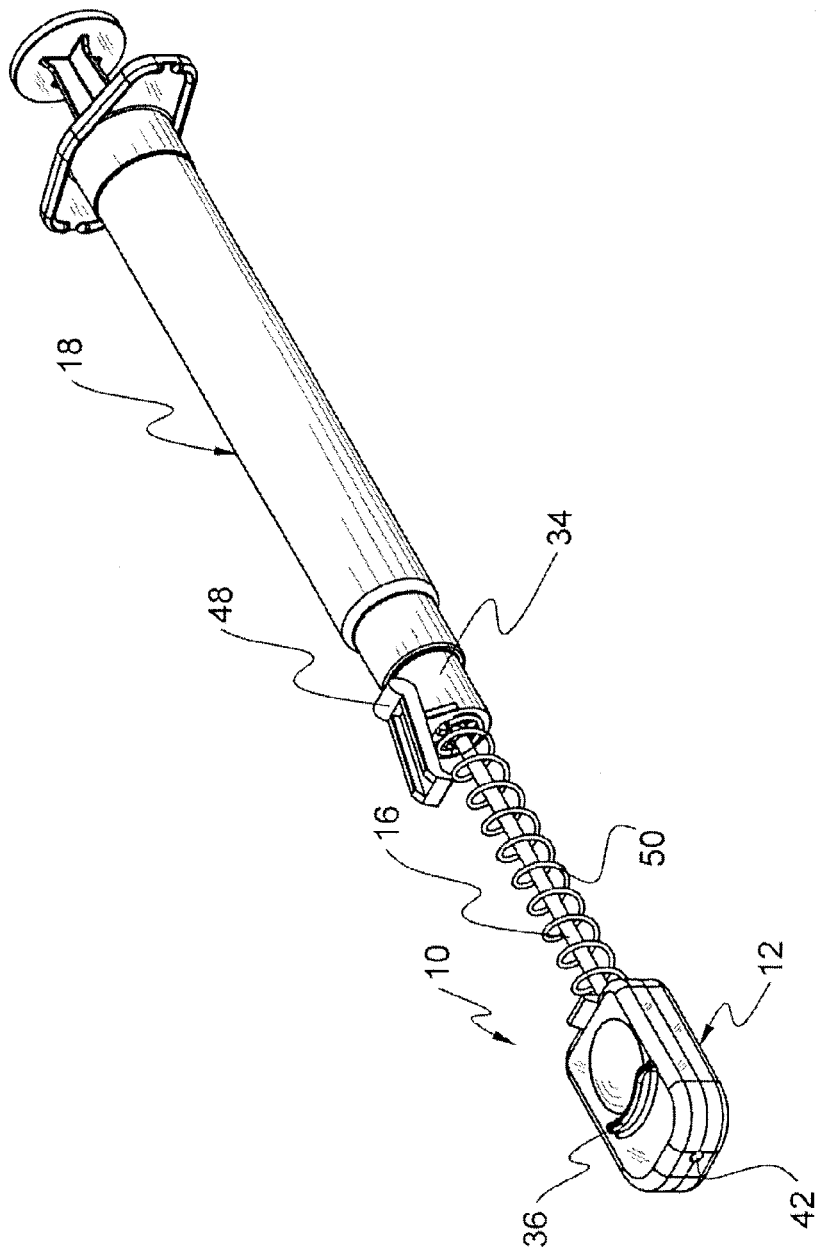
FIG. 13 is a perspective view of the medical needle shield apparatus of FIG. 12 in a post-use, shielded position.
Figure 14:
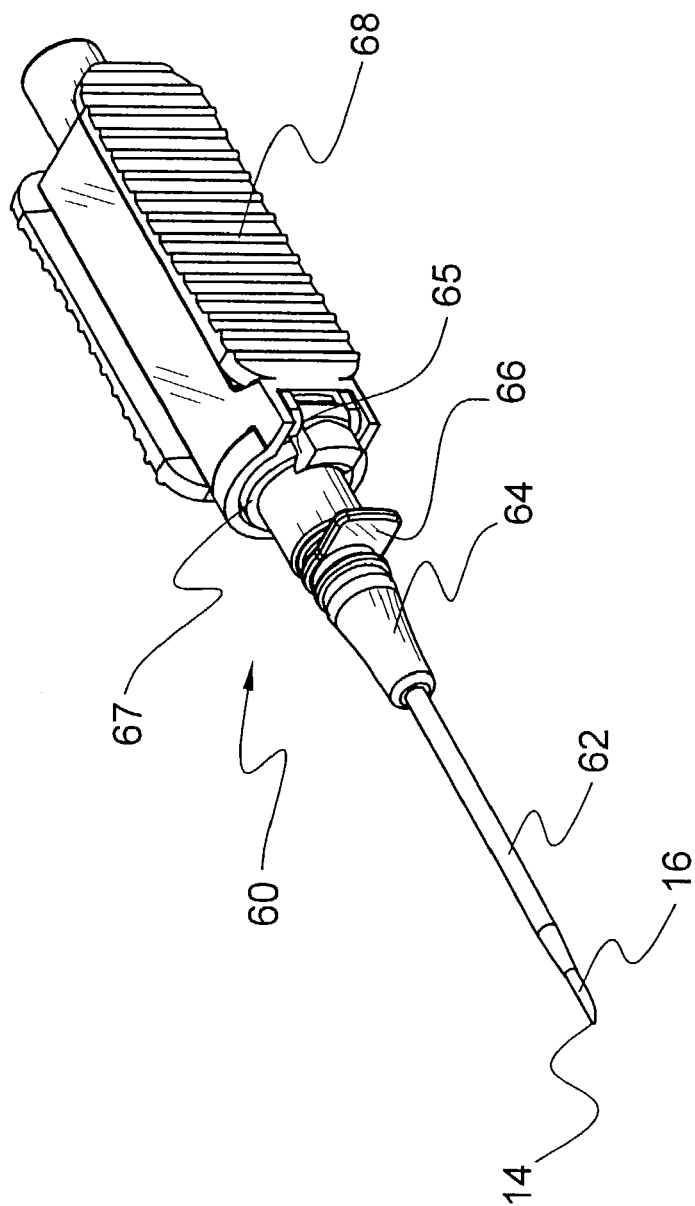
FIG. 14 is a perspective view of a medical needle shield apparatus for a catheter application.

FIGS. 12 and 13 illustrate the safety shield assembly 10 further comprising a spring 50 for moving the shield 12 from a proximal position where the distal end 14 of the needle 16 is exposed to a distal position where the shield 12 covers the distal end 14 of the needle 16. The spring 50 is held in a biased and compressed state by means of a retainer 48 which is movable to release the spring 50 from a compressed state (shown in FIG. 12) to an extended state (shown in FIG. 13). For blood collection embodiments, the retainer 48 may be activated when a blood collection tube is placed in the barrel of the blood collection device for purposes of collecting blood while the needle 16 in inserted into a patient. When the retainer 48 is activated the spring 50 moves the shield 12 along the needle 16 until it reaches a patient's skin, while the spring 50 remains in a biased condition and slightly presses the shield 12 against the patient's skin. When the needle 16 is removed from the patient, the spring 50 causes the shield 12 to continue sliding on the needle 16 to cover the distal end 14 of the needle 16, at which point the shield 12 is secured to the needle 16.

FIGS. 14–25 illustrate embodiments of the present invention as applied to a catheter needle 16. A safety shield assembly 60 for use with a catheter needle 16 having proximal and distal ends, comprises a shield 12' slidably movable along the needle 16 from a proximal position where the distal end 14 of the needle 16 is exposed, to a distal position where the shield 12' covers the distal end 14 of the needle 16. The shield 12 comprises a housing 70 with one or more clips 20' having two or more apertures 22' through which the needle 16 passes. The apertures 22' have surfaces. A clip positioning member 26' is in communication with at least one of the clips 20' for positioning the aperture surface of at least one of the clips 20' when a portion 38' of the clip positioning member 26' in contact with the needle 16' is advanced past the distal end 14 of the needle 16 such that at least a portion of the aperture surfaces of the two or more apertures 20' binds to the needle 16 with opposing binding forces so as to secure the shield 12' to the needle 16. A reaction force element 74 may be added to apply a binding force of the clip 20' on the needle 16. Reaction force element 74 serves the same function as clip support 44. The safety shield assembly further comprises a catheter 62, wherein the catheter 62 affixed to hub 64 is held to the shield 12' with a retainer 65 in communication with the clip positioning member 26' until the portion 28' of the clip positioning member 26' in contact with the needle 16 is advanced past the,distal end 14 of the needle 16 upon which the retainer 65 is repositioned to release the catheter 62 and hub 64 from the shield 12'. FIGS. 14–20 show an embodiment-in which the retainer 65 retains to the hub 64 by means of a flanged surface 67. However, numerous cooperating catches and latches fall within the scope of the present invention to accomplish the intended function of a catch and latch.

FIGS. 21–24 illustrate embodiments of the present invention as applied to a catheter needle apparatus having a clip 20" and clip positioning member 26" as one continuous member.

Figure 15:
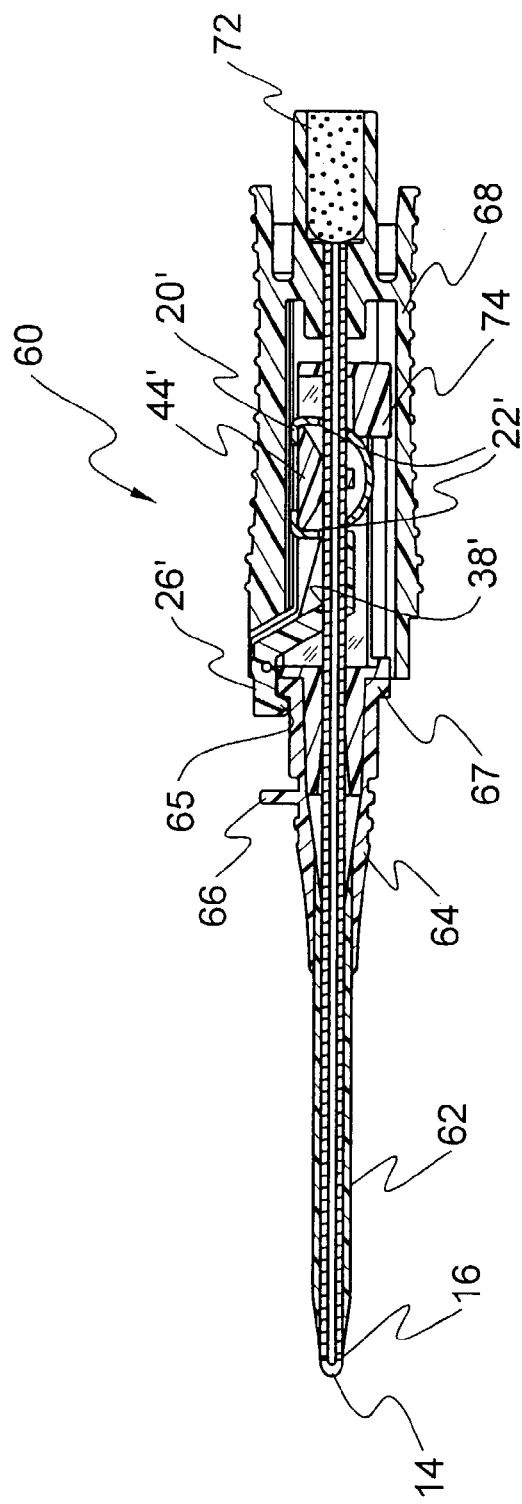
FIG. 15 is a lateral cross sectional view of the medical needle shield apparatus of FIG. 14.
Figure 16:
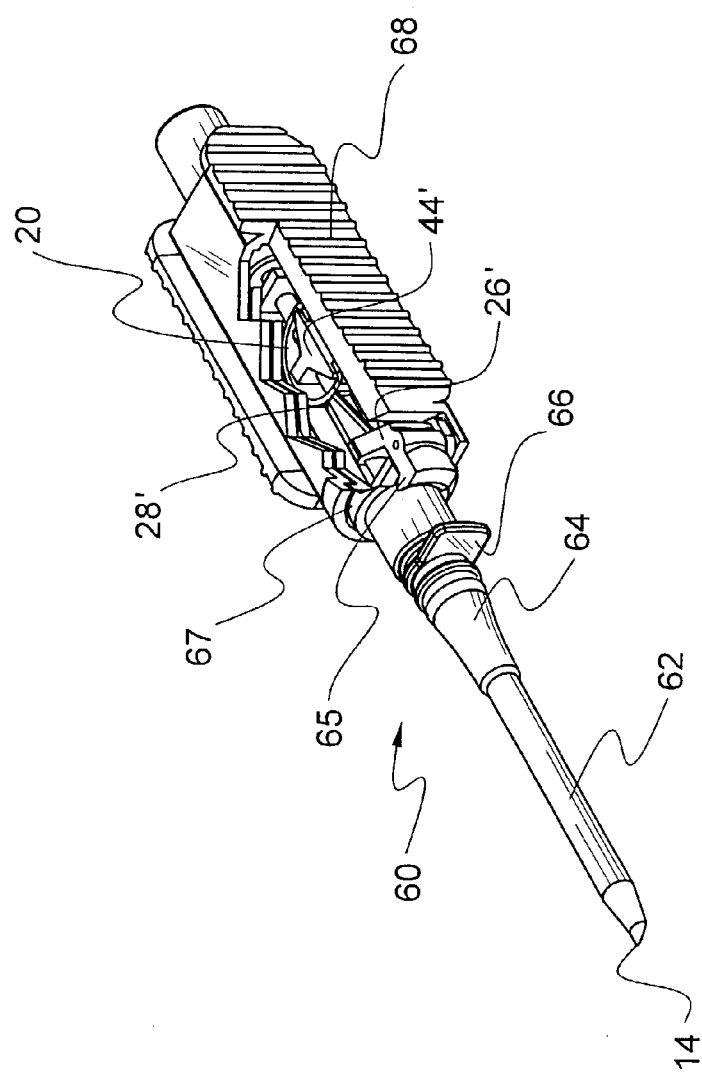
FIG. 16 is a perspective view of a medical needle shield apparatus of FIG. 14 with a cut-out view of inner components.
Figure 17:
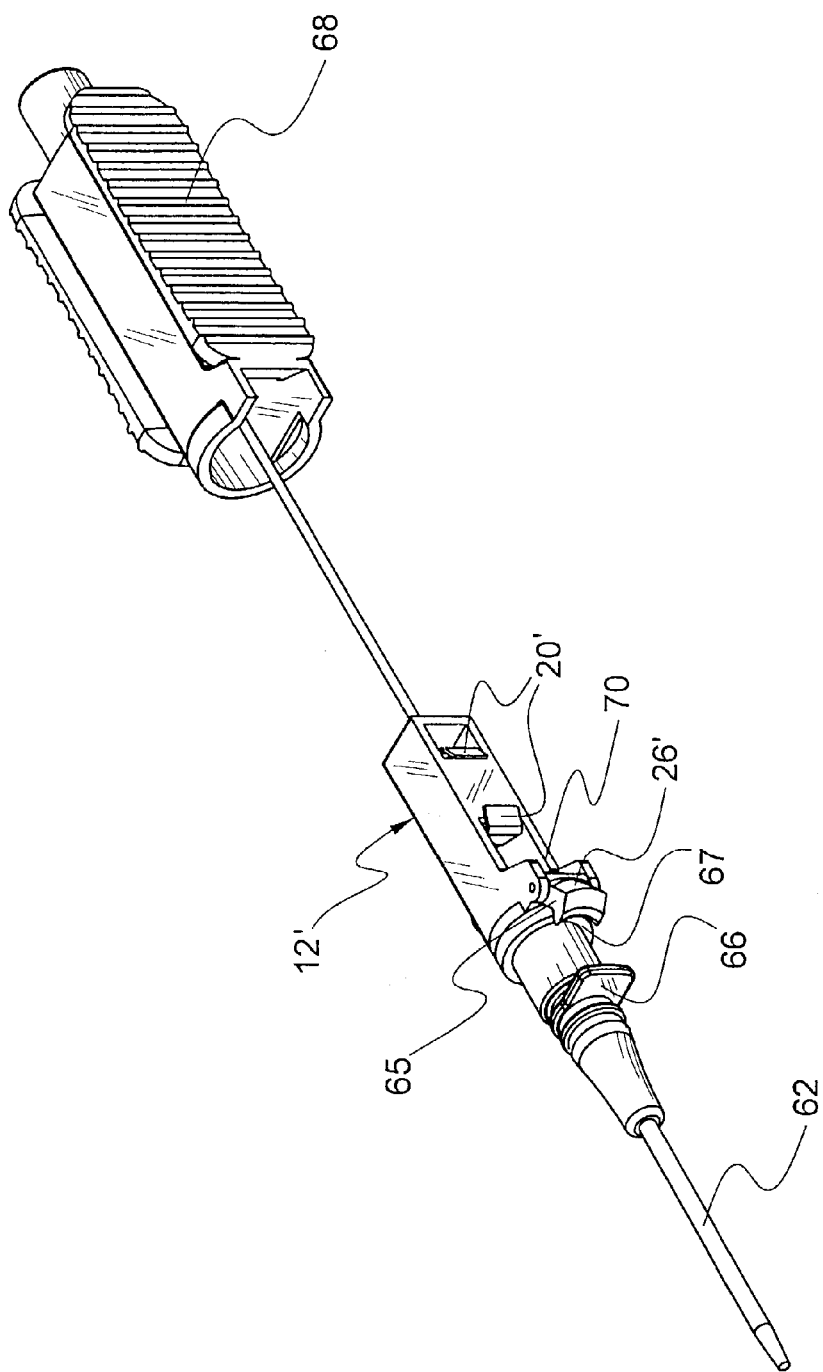
FIG. 17 is a perspective view of the medical needle shield apparatus of FIG. 14 as a needle shield assembly is being moved to the distal end of a needle just prior to the release of a catheter attached to a catheter hub.
Figure 18:
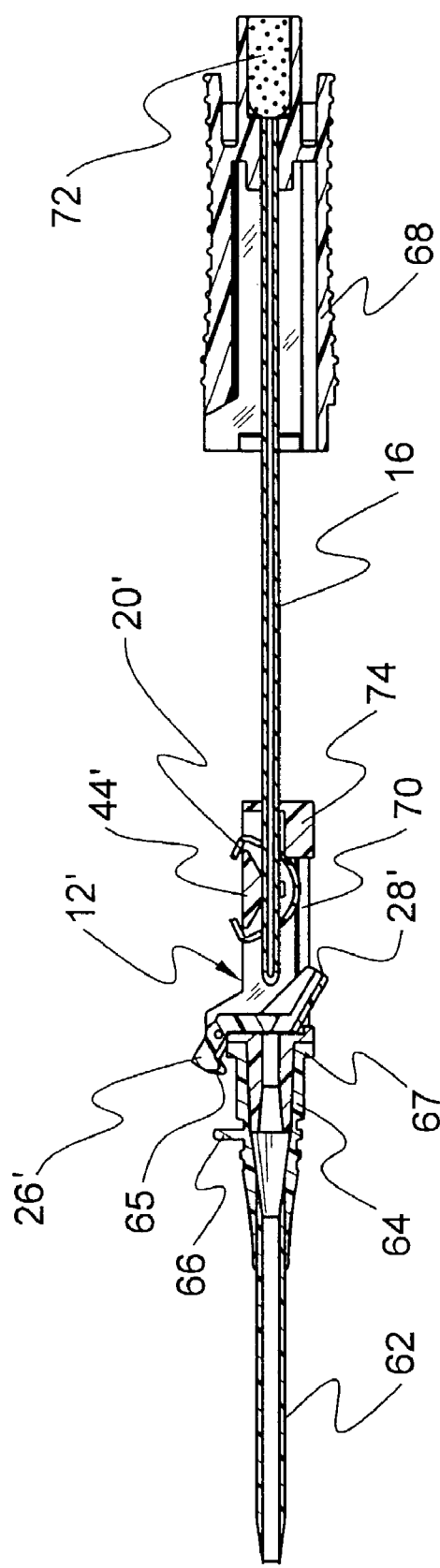
FIG. 18 is a lateral cross sectional view of the medical needle shield apparatus of FIG. 17.
Figure 19:
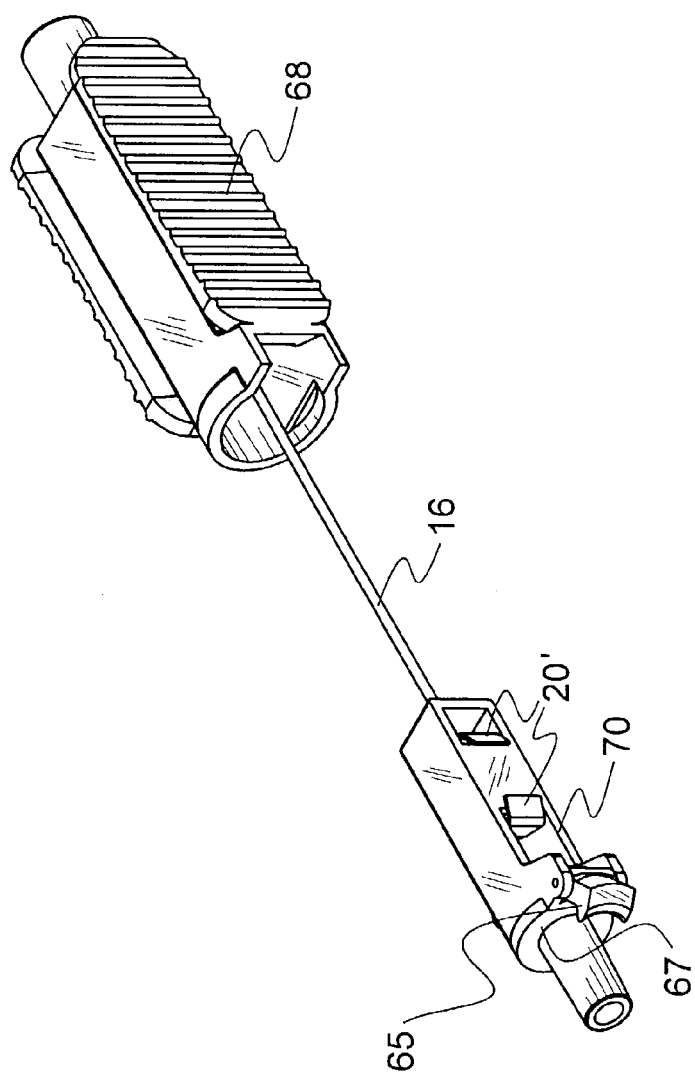
FIG. 19 is a perspective view of the medical needle shield apparatus of FIG. 14 as a shield assembly is locked to a needle and a catheter and catheter hub (shown in FIG. 18) have been released.
Figure 20:
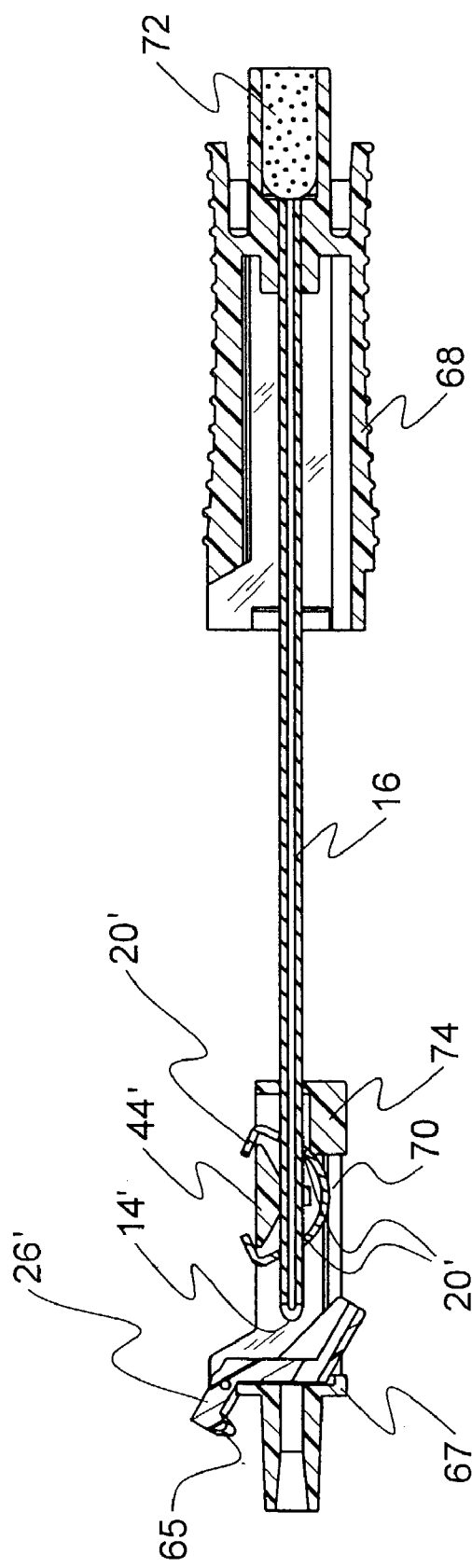
FIG. 20 is a lateral cross sectional view of the medical needle shield apparatus of FIG. 19.
Figure 21:
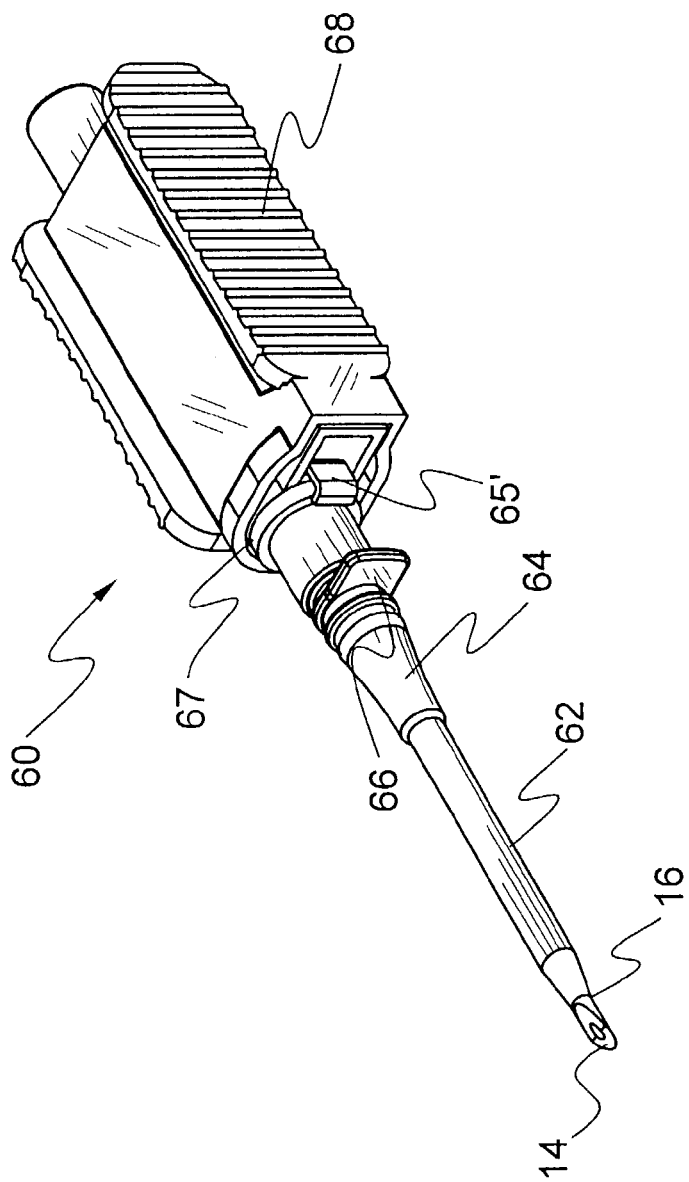
FIG. 21 is a perspective view of a medical needle shield apparatus for a catheter application having a clip and clip positioning member as one continuous part.
Figure 22:
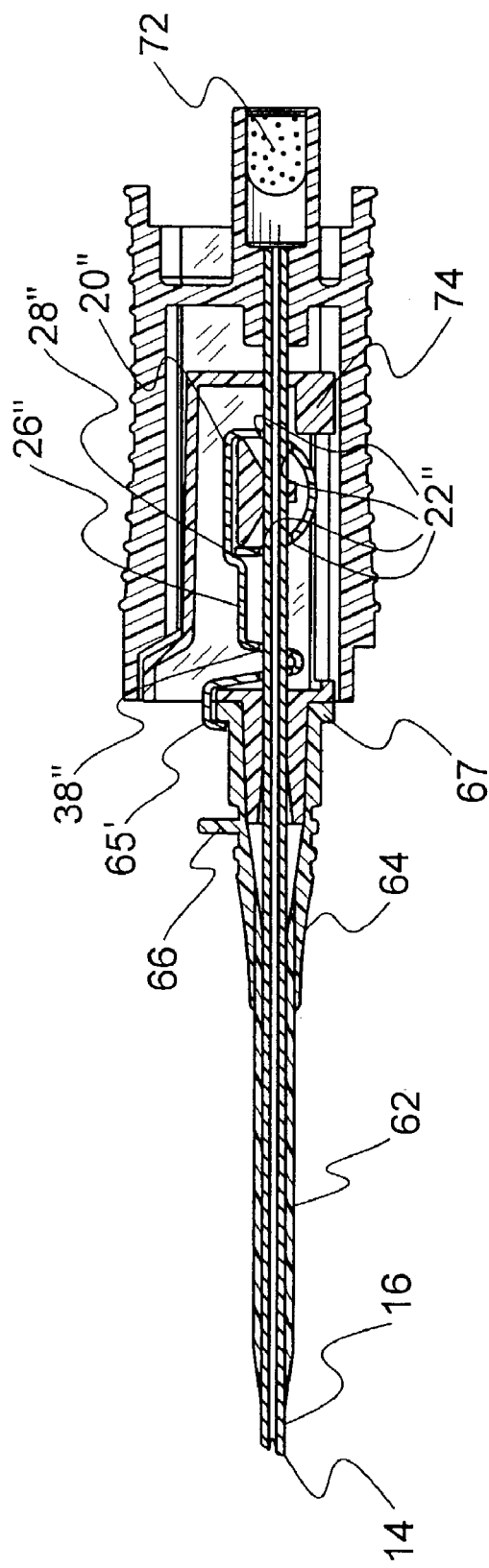
FIG. 22 is a lateral cross sectional view of the medical needle shield apparatus of FIG. 21.
Figure 23:
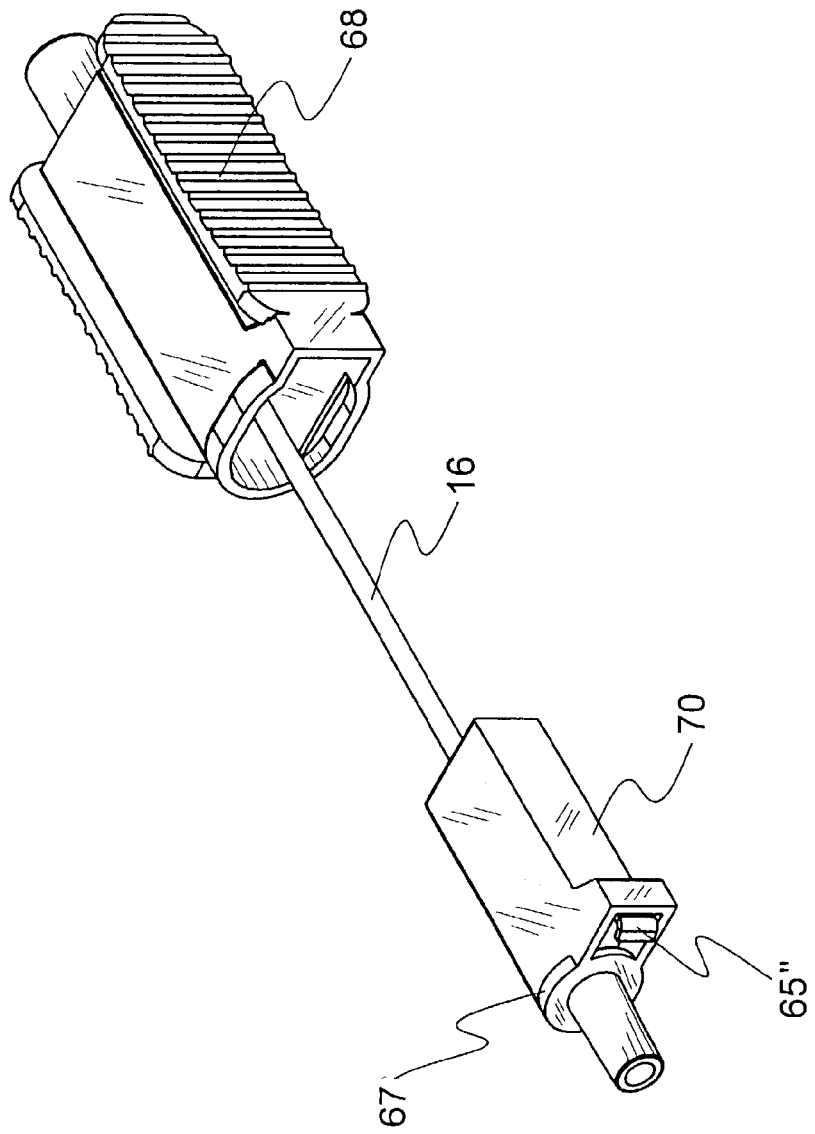
FIG. 23 is a perspective view of the medical needle shield apparatus of FIG. 21 as a shield assembly is locked to a needle and a catheter and catheter hub (shown in FIG. 21) have been released.
Figure 24:
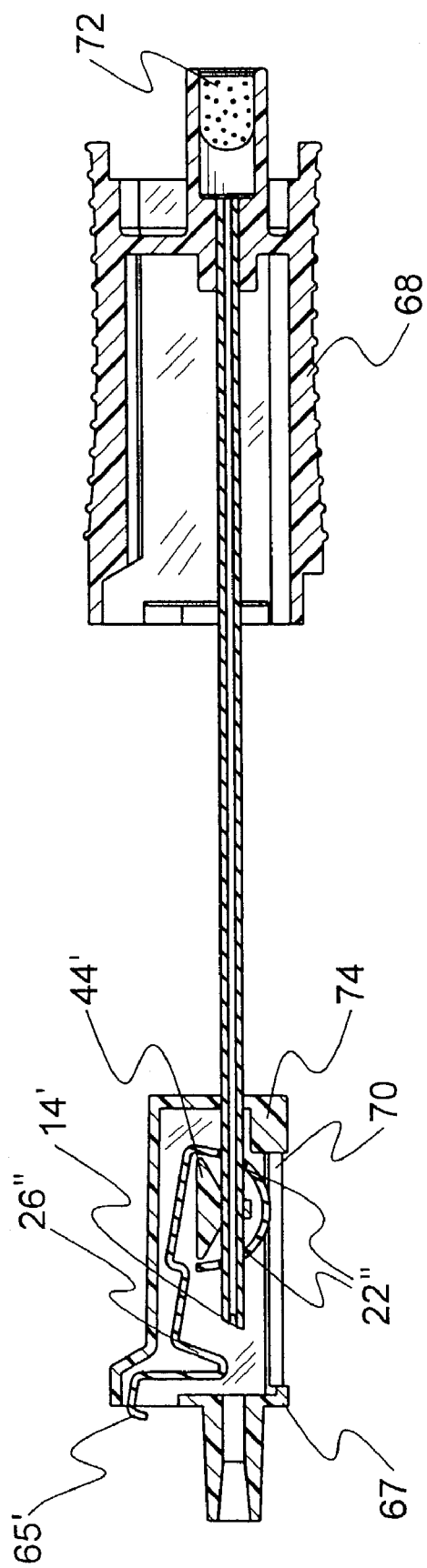
FIG. 24 is a lateral cross sectional view of the medical needle shield apparatus of FIG. 23.

As shown in FIGS. 15 and 22, a hydrophobic filter 72 may be housed in the safety shield assembly 60.

A tab 66 may be disposed on the catheter hub 64 for assisting in moving the catheter 62 and hub 64 axially along the needle 16 as a health care worker presses against the tab 66 with a finger, while holding the catheter introducer handle 68.

Figure 25:
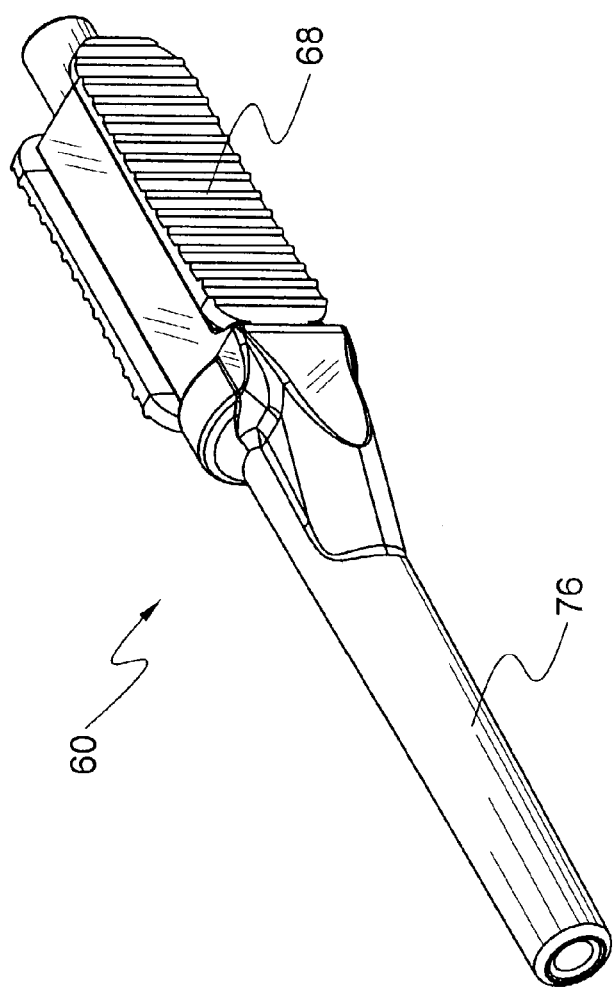
FIG. 25 is a perspective view of the medical needle shield apparatus of FIG. 14 with a needle cover placed over the needle prior to use.

As shown in FIG. 25 for a catheter embodiment, a needle cover 76 is commonly used to protect needles 16 prior to use and to prevent inadvertent actuation of the safety shield assembly 60 before cover 76 is removed for use of the catheter 62.

Figure 26:
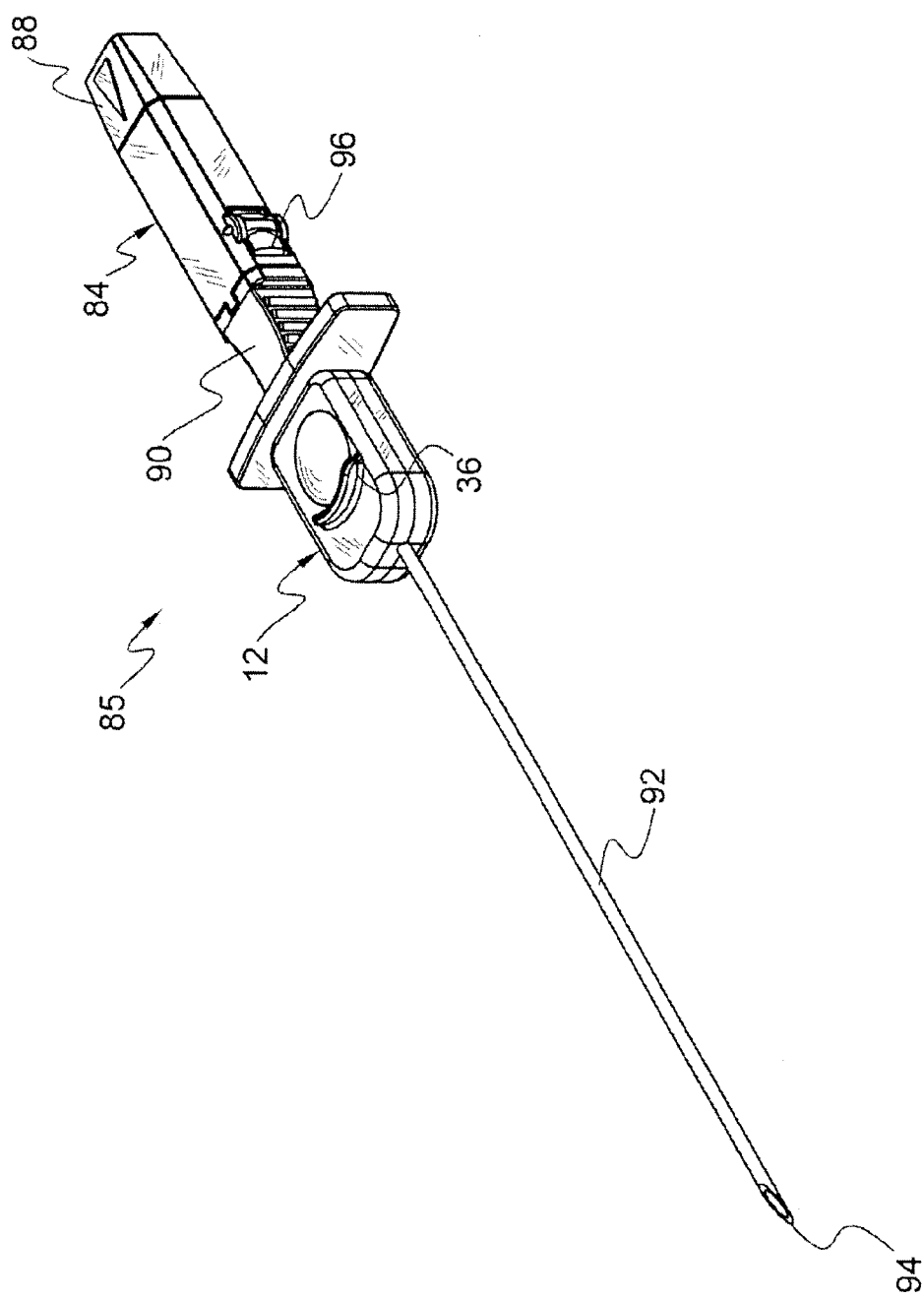
FIG. 26 is a perspective view of a medical needle shield apparatus for an epidural or biopsy needle application in a pre-use condition.

FIGS. 26–31 illustrate safety devices for needle applications having an introducer needle 92 and an inner needle 86 for applications including, but not limited to, epidural and biopsy needles. Tubular or solid inner needles 86 are within the scope of the present invention. The safety shield assembly 85 shown in FIG. 26 is for use with a needle 92 having a proximal end (not shown) and a distal end 94. The shield assembly 85 comprises a shield 12 (similar to the shield shown in FIGS. 1–9) slidably movable along the needle 92 from a proximal position where the distal end 94 of the needle 92 is exposed, to a distal position where the shield 12 covers the distal end 12 of the needle 92. The shield 12 comprises one or more clips 20 having two or more apertures 22 (see FIGS. 1–9) through which the needle 92 passes. The apertures 22 have surfaces 24 which contact the needle 92. A clip positioning member 26 is in communication with at least one of the clips 20 for positioning the aperture surface 24 of at least one of the clips 20 when a portion 38 of the clip positioning member 26 in contact with the needle 92 is advanced past the distal end 94 of the needle 92 such that at least a portion of the aperture surfaces 24 of the two or more apertures 22 binds to the needle 92 with opposing binding forces so as to secure the shield 12 to the needle 92. An introducer needle handle 90 aids in the insertion of introducer needle 92. The front side of the introducer needle handle 90 is connected to the introducer needle 92. As shown in FIGS. 1–6, the clip 20 may be integrally connected with the clip positioning member 26, wherein the clip is held in a biased state by a retention surface 28 disposed on the clip positioning member 26. FIGS. 1–6 show the shield 12 further comprising a housing having an upper portion 30 and a lower portion 32 for encapsulating the shield 12.

Figure 27:
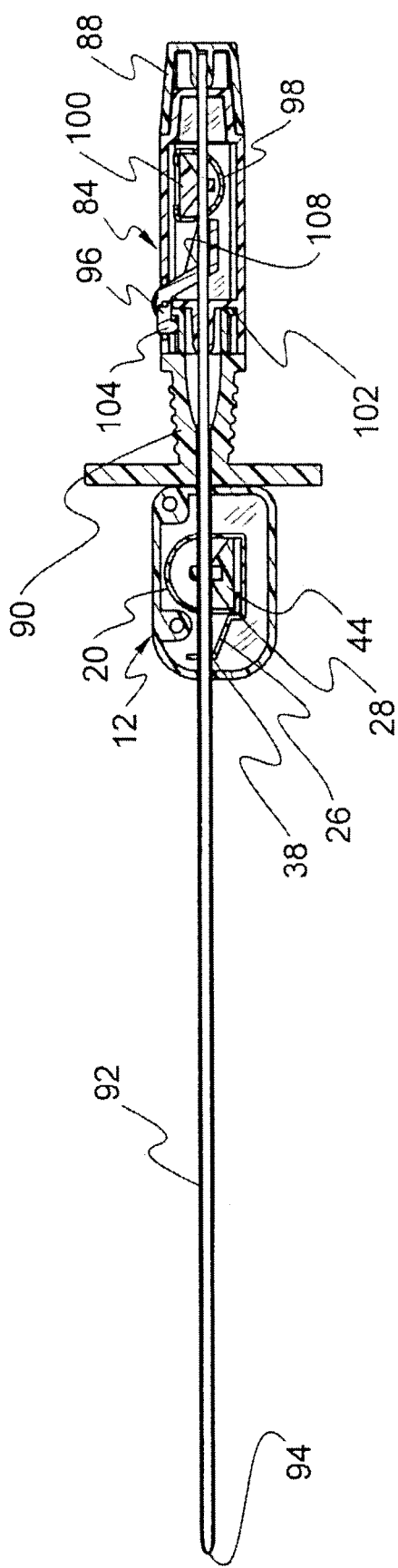
FIG. 27 is a lateral cross sectional view of the medical needle shield apparatus of FIG. 26.
Figure 28:
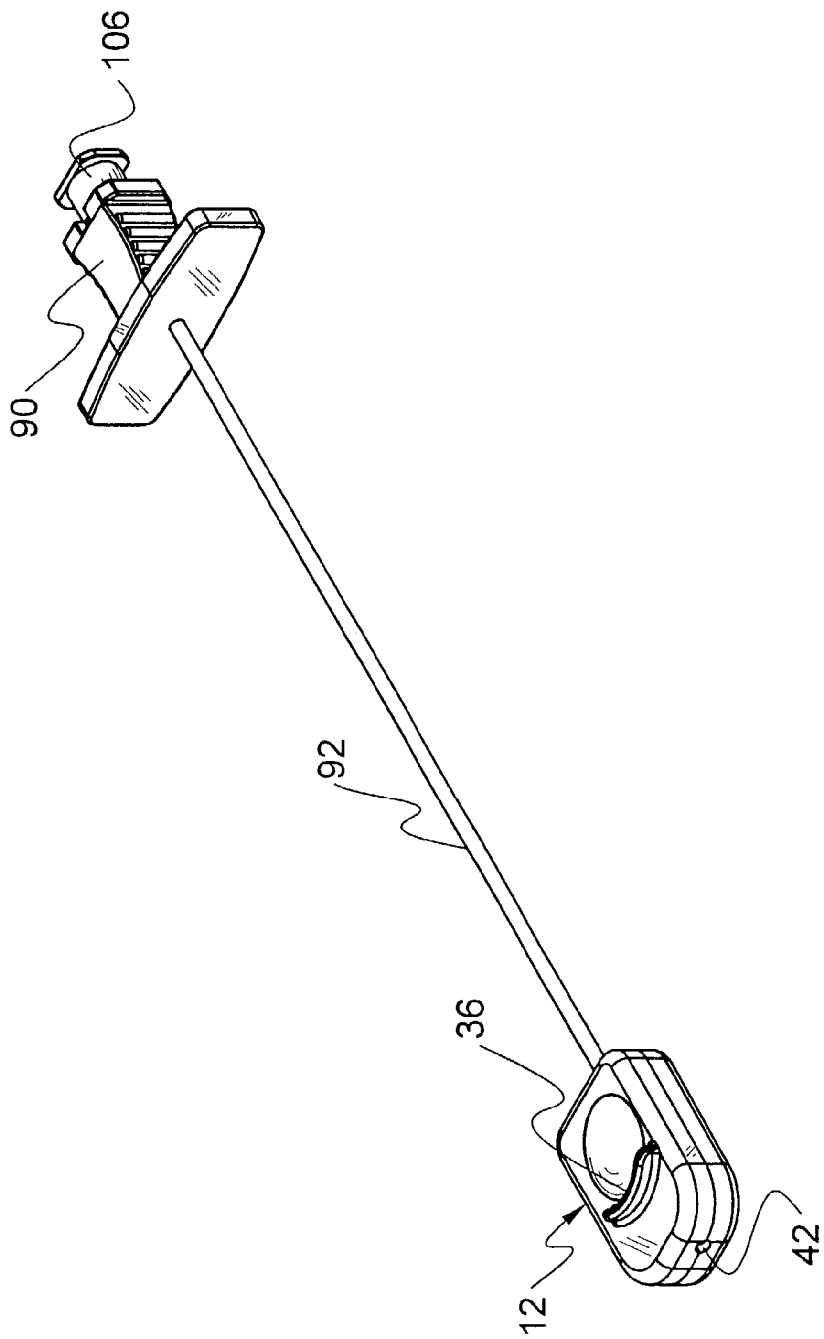
FIG. 28 is a perspective view of a medical needle shield apparatus for an epidural or biopsy needle application in a post-use condition.
Figure 30:
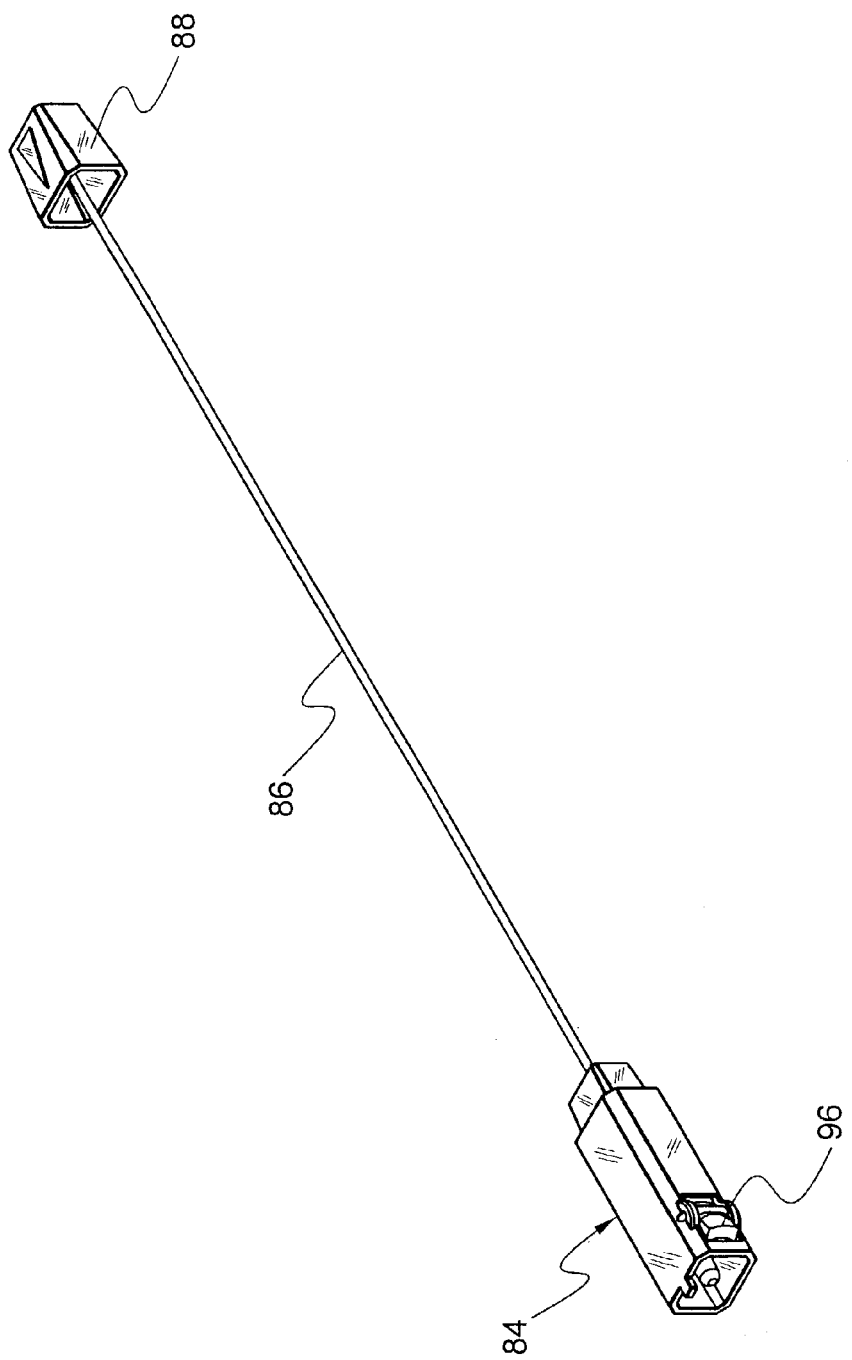
FIG. 30 is a perspective view of the inner needle shield apparatus for the device shown in FIG. 28.

FIGS. 26 and 27 show the safety shield assembly 85 in a pre-use state, while FIGS. 28 and 29 show the post-use and protected state. FIGS. 30 and 31 show an inner needle shield 84 protecting the distal end 87 of inner needle 86 (e.g., stylet of a biopsy needle) in the post-use and protected state. The inner needle 86 is attached to a hub 88 in communication with the inner needle shield 84 as shown in FIGS. 26 and 27. A luer fitting 106, as shown in FIGS. 28 and 29, allows for attachment to a syringe or like device.

The inner needle shield 84 is slidably movable along the inner needle 86 from a proximal position to a distal position where the inner needle shield 84 covers the distal end 87 of the inner needle 86 as the inner needle 86 is withdrawn from the needle 92. The inner needle shield 84 comprises one or more clips 98 having two or more apertures (similar to apertures 22 previously disclosed) through which the inner needle 86 passes. FIGS. 27 and 31 illustrate clip 98 being supported by a clip support 100. The apertures have surfaces (similar to aperture surfaces 24 disclosed previously) which contact the needle 92. A clip positioning member 96 is in communication with at least one of the clips 98 for positioning the aperture surface of at least one of the clips 98 when a portion 108 of the clip positioning member 96 in contact with the inner needle 86 is advanced past the distal end 87 of the needle 86 such that at least a portion of the aperture surfaces of the two or more apertures binds to the needle 86 with opposing binding forces so as to secure the inner needle shield 84 to the needle 86. The inner needle shield 84 further comprises a retainer 104 for holding the inner needle shield 84 to the back side of the introducer needle handle 90, wherein retainer 104 is in communication with the clip positioning member 96 until the portion 108 of the clip positioning member 96 in contact with the inner needle 86 is advanced past the distal end 87 of the inner needle 86 upon which the retainer 104 is repositioned to release the inner needle shield 84 from the introducer needle handle 90. Hence, the inner shield 84 is passively activated upon withdrawal of inner needle 86 from the introducer needle handle 90. FIG. 27 shows the retainer 104 in communication with the clip positioning member 96 along a flanged surface 102. Alternatively, the inner needle shield 84 and retainer 104 may comprise cooperating detents and detent pockets for mutually engaging to hold the inner needle shield 84 to the introducer needle handle 90. However, numerous cooperating catches and latches fall within the scope of the present invention to accomplish the intended function of a catch and latch.

Figure 32:
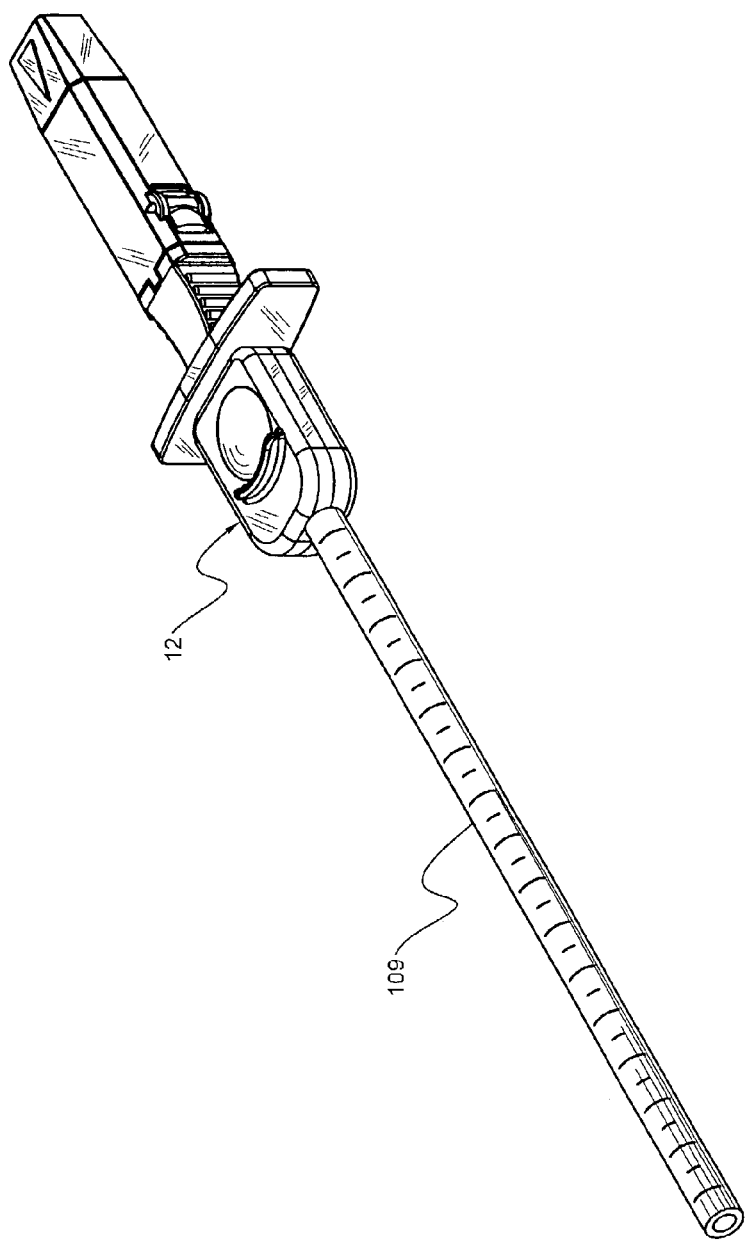
FIG. 32 is a perspective view of the device shown in FIG. 26, wherein the shield also serves as a needle insertion depth indicator.

FIG. 32 shows a biopsy needle having a needle protective cover 109 with a measuring scale for determining a desired insertion depth. Using protective cover 109 to measure the desired insertion depth, shield 12 may then be placed at a position along the needle to indicate the desired insertion depth position.

Figure 33:
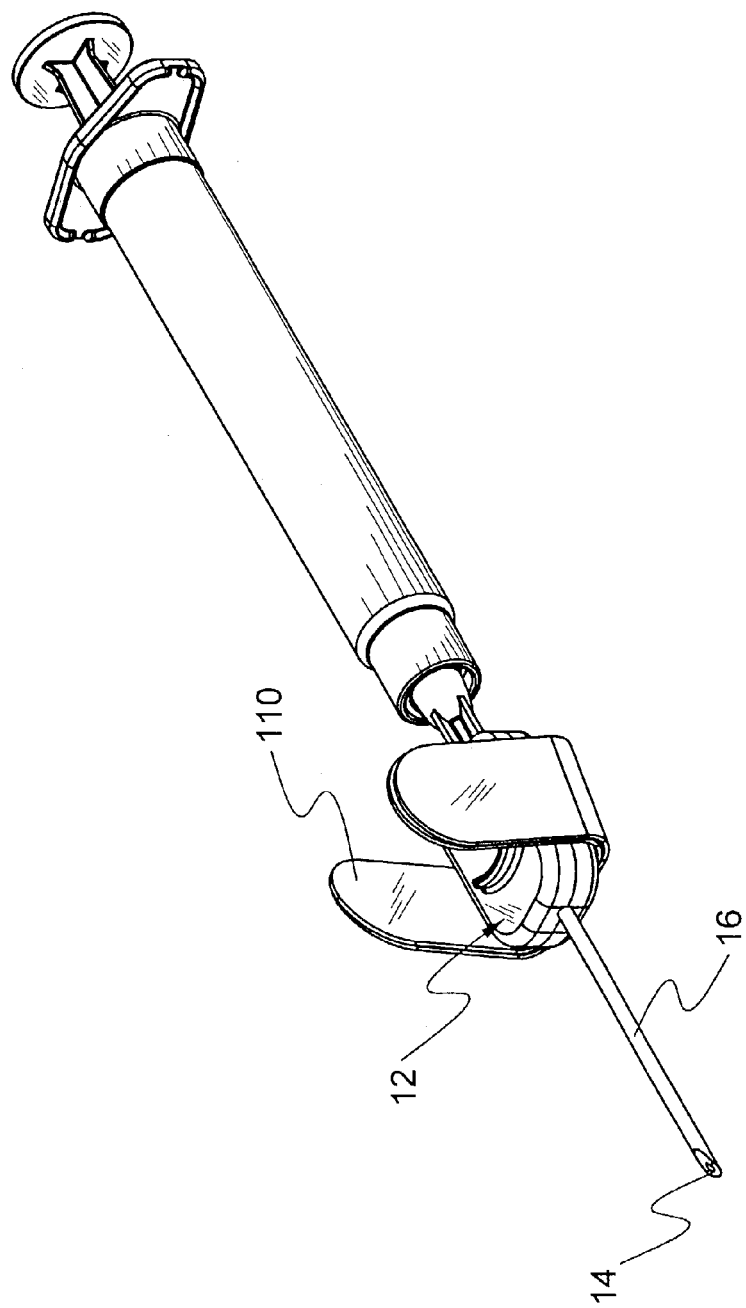
FIG. 33 is a perspective view of a medical needle shield apparatus having a releasably attached tape down member in a pre-use condition.
Figure 34:
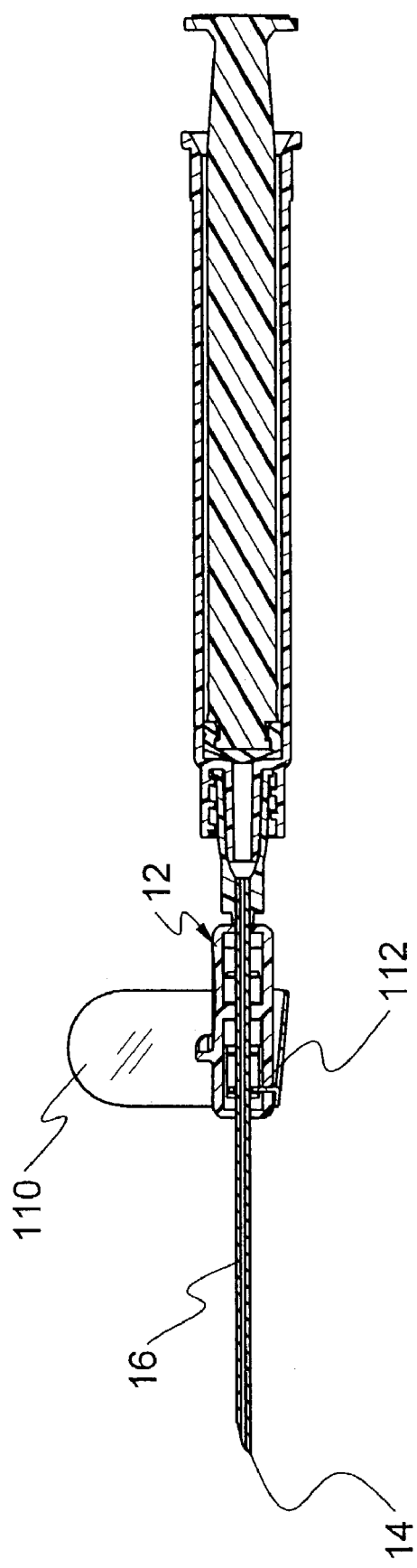
FIG. 34 is a lateral cross sectional view of the medical needle shield apparatus of FIG. 33.
Figure 35:
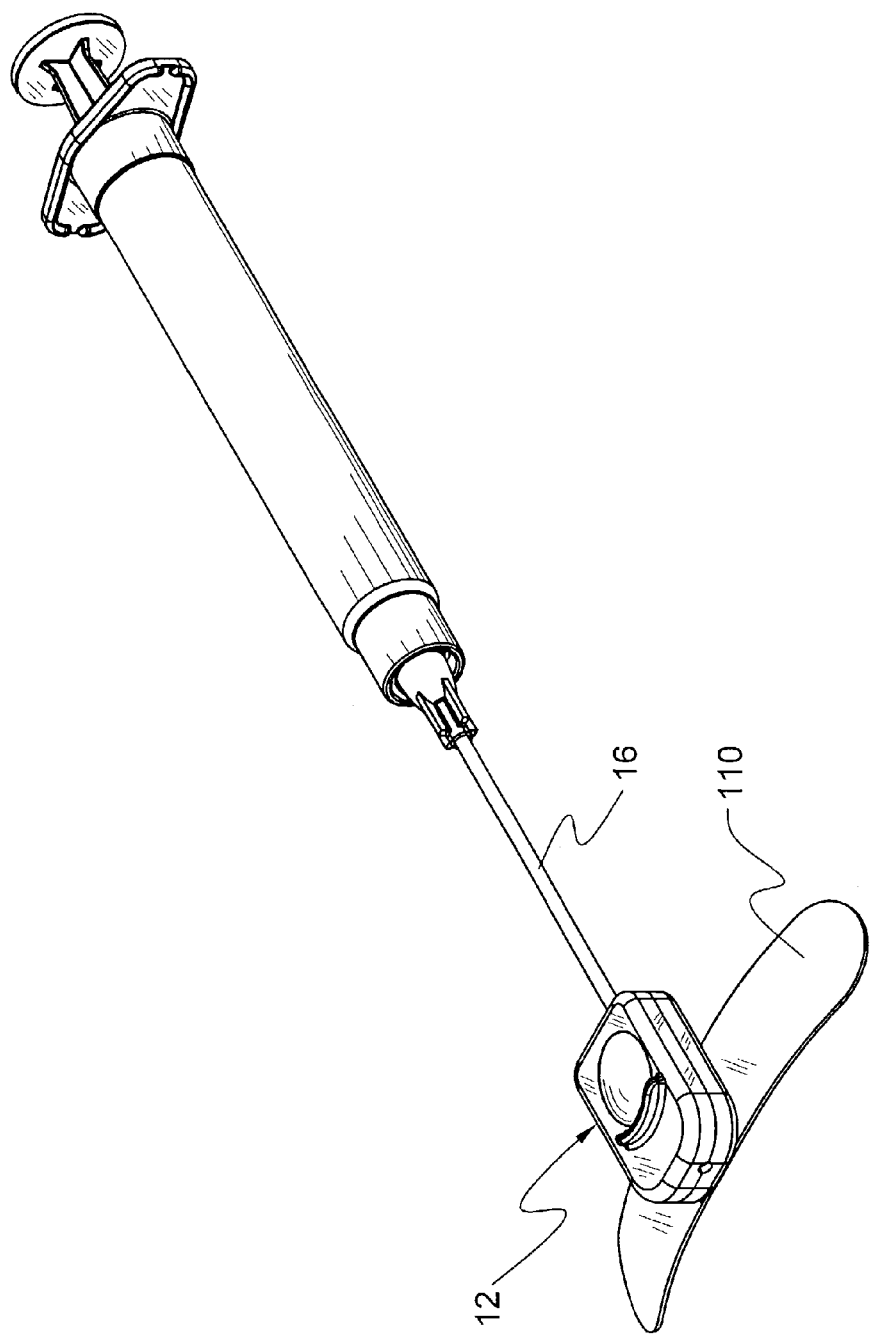
FIG. 35 is a perspective view of a medical needle shield apparatus having a releasably attached tape down member in a post-use condition.
Figure 36:
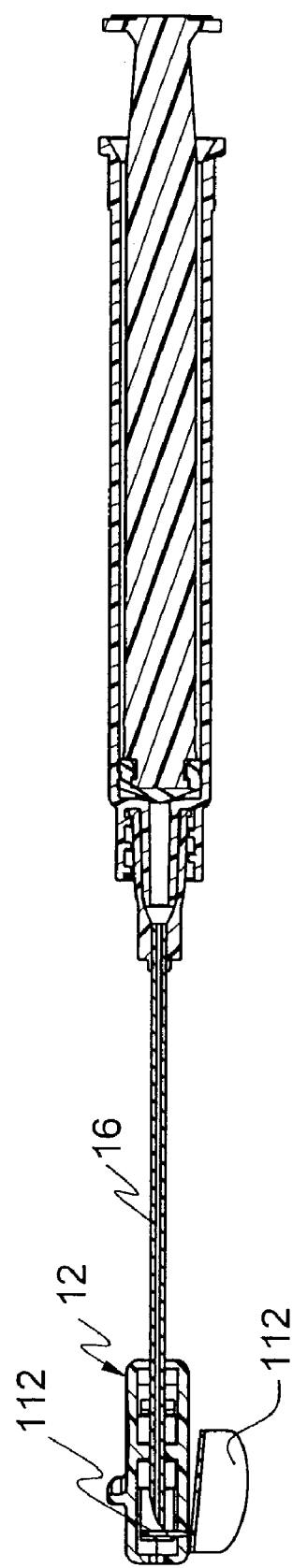
FIG. 36 is a lateral cross sectional view of the medical needle shield apparatus of FIG. 35.
Figure 37:
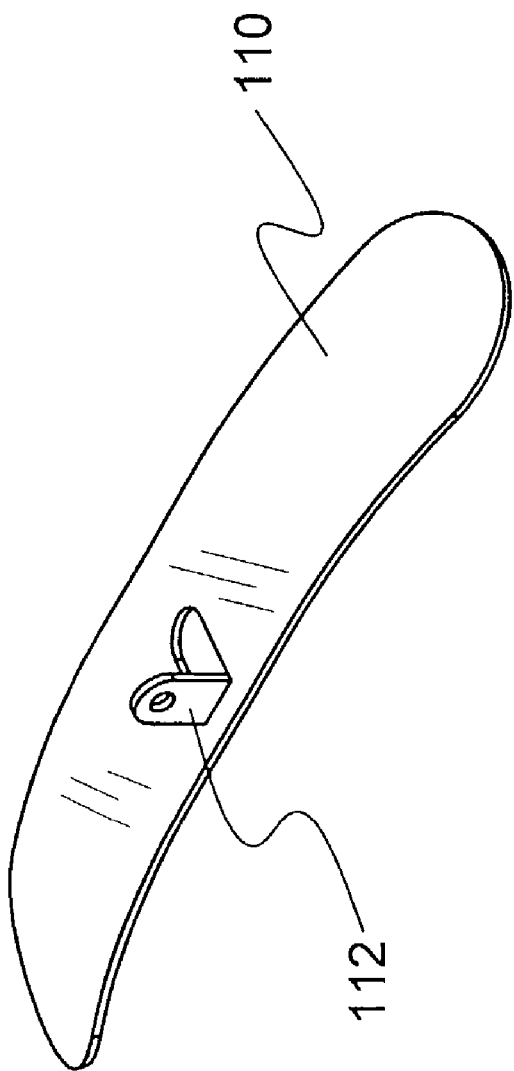
FIG. 37 is a view of the tape down member of FIGS. 33–36 in isolation.

FIGS. 33–37 show an embodiment of the present invention incorporating a tape down 110 member which releases from the shield 12 as a portion 112 of the tape down member 110 in contact with the needle 16 is advanced past the distal end 14 of the needle 16. However, there are a number of methods of releasably attaching the tape down member 110 to the shield 12 which fall within the scope of the present invention. FIGS. 33 and 34 show the safety shield 12 in a pre-use state, while FIGS. 35 and 36 show the post-use and protected state. FIG. 37 shows the tape down member 110 in isolation. The tape down member 110 may be taped to a patient using separate tape or, alternatively, tape down member 110 may have an adhesive disposed on its underside.

Figure 38:
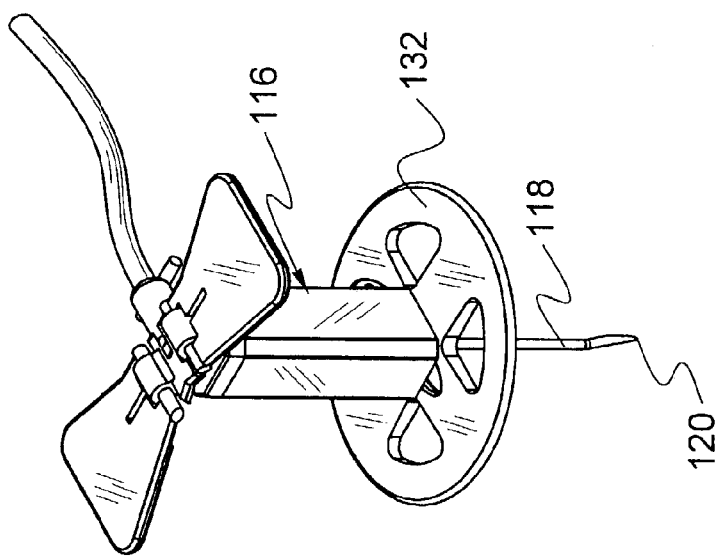
FIG. 38 is a perspective view of a medical needle shield apparatus for a port access needle application in a pre-use condition.
Figure 39:
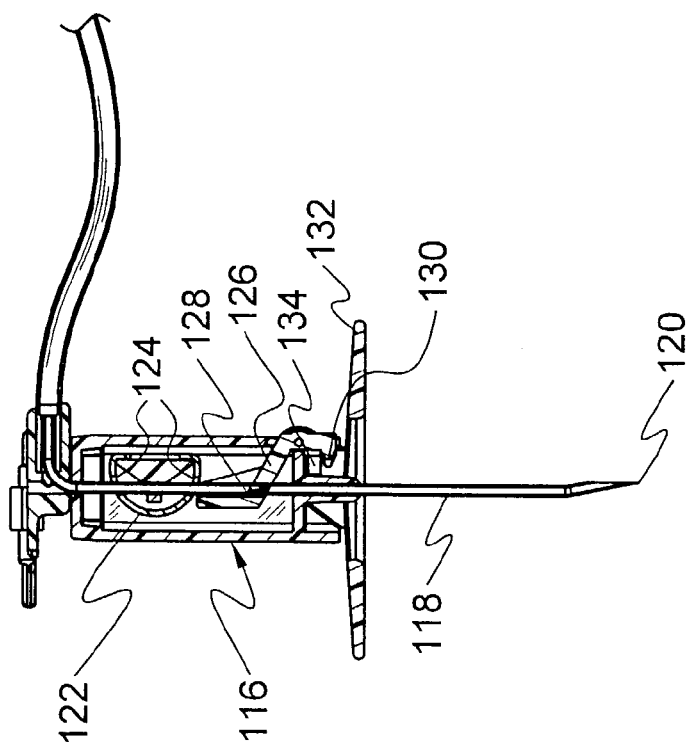
FIG. 39 is a lateral cross sectional view of the medical needle shield apparatus of FIG. 38.
Figure 40:
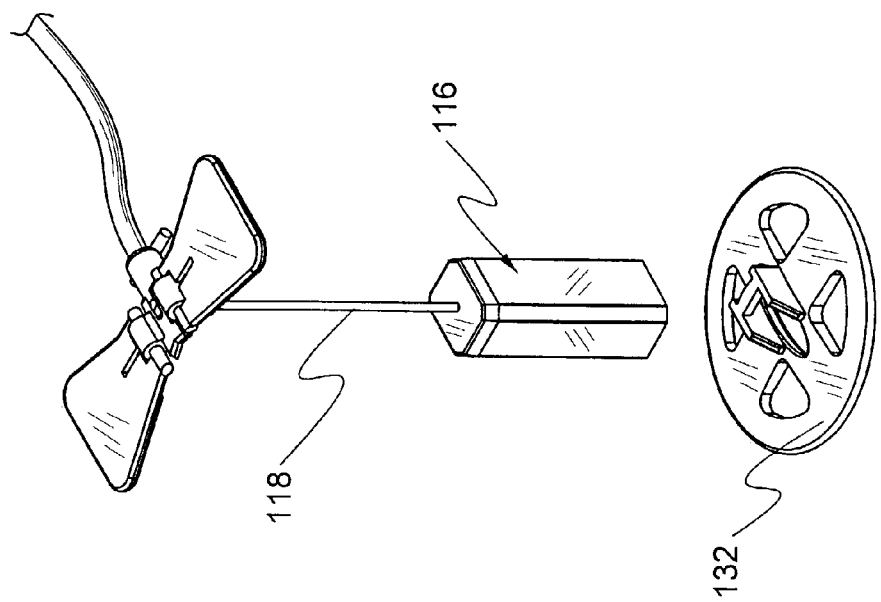
FIG. 40 is a perspective view of a medical needle shield apparatus for a port access needle application in a post-use condition.
Figure 41:
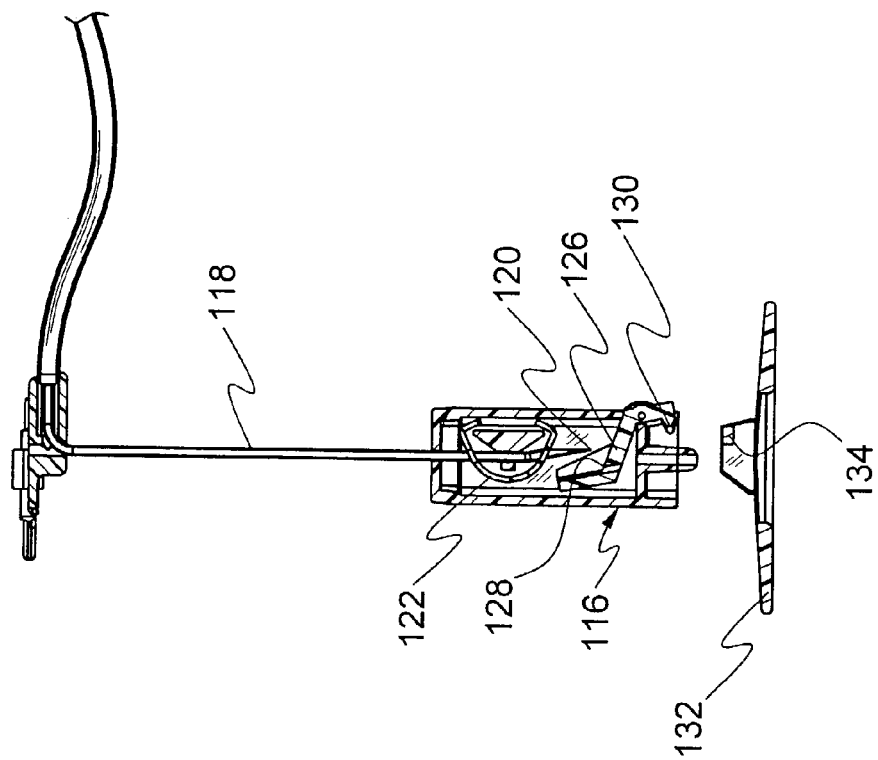
FIG. 41 is a lateral cross sectional view of the medical needle shield apparatus of FIG. 40.

FIGS. 38–41 illustrate embodiments for a port access needle 118. FIGS. 38 and 39 show the safety shield assembly 116 in a pre-use state, while FIGS. 40 and 41 show the post-use and protected state. As shown in FIG. 38, the safety shield 116 for use with a port access needle 118 is slidably movable along the needle 118 from a proximal position where the distal end 120 of the needle 118 is exposed, to a distal position where the shield 116 covers the distal end 120 of the needle 118. The shield 116 comprises one or more clips 122 having two or more apertures 124 through which the needle 118 passes. The apertures 124 have surfaces (similar to aperture surfaces 24 disclosed previously) which contact the needle 118. A clip positioning member 126 is in communication with at least one of the clips 122 for positioning the aperture surface of at least one of the clips 122 when a portion 128 of the clip positioning member 126 in contact with the needle 118 is advanced past the distal end 120 of the needle 118 such that at least a portion of the aperture surfaces of the two or more apertures 124 binds to the needle 118 with opposing binding forces so as to secure the shield 116 to the needle 118. The shield 116 further comprises a retainer 130 for holding the shield 116 to the disk 132, wherein the retainer 130 is in communication with the clip positioning member 126 until the portion 128 of the clip positioning member 126 in contact with the needle 118 is advanced past the distal end 120 of the needle 118 upon which the retainer 130 is repositioned to release the shield 116 from the disk 132. Hence, the shield 116 is passively activated upon withdrawal of the needle 118 from the disk 132. FIG. 39 shows the retainer 130 in communication with the clip positioning member 126 along a flanged surface 134. Alternatively, the shield 116 and retainer 130 may comprise cooperating detents and detent pockets or cooperating catches and latches for mutually engaging to hold the shield 116 to the disk 132.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a shield being movable along a needle between a proximal position, whereby a distal end of the needle is exposed, and a distal position, whereby the shield encloses the distal end of the needle;
   a clip disposed within the shield and defining a first aperture and a second aperture through which the needle passes, the first aperture and the second aperture defining binding surfaces configured to engage the needle; and
   a clip positioning member disposed with the clip, the clip positioning member having a retention surface disposed at a first end thereof that is configured to engage the clip and a needle engaging surface, the needle engaging surface engaging the needle and the retention surface engaging the clip to maintain the clip in a biased state, the needle engaging surface being distally movable past the distal end of the needle such that the retention surface is releasable from engagement with the clip thereby disposing the clip in an unbiased state such that the binding surfaces engage the needle within the shield,
   a retainer extending from the clip positioning member and being configured to engage a flange of a medical needle device.

2. The medical needle shield apparatus according to claim 1, wherein the clip and clip positioning member are monolithically formed such that the clip positioning member extends from the clip.

3. The medical needle shield apparatus according to claim 1, wherein the needleshield apparatus further comprises additional shield.

4. The medical needle shield apparatus according to claim 1, wherein the needleshield apparatus includes an additional clip and an additional corresponding clip positioning member.

5. The medical needle shield apparatus according to claim 1, wherein the clip defines an inner cavity and the shield includes a support, the support being disposed within the inner cavity of the clip for positioning the clip.

6. The medical needle shield apparatus according to claim 1, wherein the clip defines an inner cavity and the shield includes a reaction force element, the reaction force element being disposed outside the inner cavity and engages the clip in a configuration to increase binding of the binding surfaces of the clip on the needle.

7. The medical needle shield apparatus according to claim 1, wherein a hydrophobic filter is mounted with the shield adjacent a proximal end of the needle.

8. The medical needle shield apparatus according to claim 1, wherein the medical needle device is a catheter.

9. The medical needle shield apparatus according to claim 1, further comprising a tape down member releasably attached to the shield.

10. The medical needle shield apparatus according to claim 1, wherein medical needle device includes an introducer needle handle connected to an outer needle disposed for movement about the needle.

11. The medical needle shield apparatus according to claim 10, wherein the introducer needle handle is connected to a second shield for use with the outer needle, the second shield being slidably movable along the outer needle from a proximal position to a distal position where the second shield covers a distal end of the outer needle.

12. The medical needle shield apparatus according to claim 1, further comprising a cover that mounts about the needle, the cover including a needle insertion depth indicator.

13. The medical needle shield apparatus according to claim 1, wherein the needle includes a port access needle.

14. The medical needle shield apparatus according to claim 1, wherein the medical needle device includes a disk that is releasably retained in engagement with the shield.

15. A medical needle shield apparatus comprising:
a shield being movable along a needle between a proximal position, whereby a distal end of the needle is exposed, and a distal position, whereby the shield encloses the distal end of the needle; and
a clip disposed within the shield and defining a first aperture and a second aperture through which the needle passes, the first aperture and the second aperture defining binding surfaces configured to engage the needle;
a clip positioning member disposed with the clip, the clip positioning member having a retention surface disposed at a first end thereof that is configured to engage the clip and a needle engaging surface, the needle engaging surface engaging the needle and the retention surface engaging the clip to maintain the clip in a biased state, the needle engaging surface being distally movable past the distal end of the needle such that the retention surface is releasable from engagement with the clip thereby disposing the clip in an unbiased state such that the binding surfaces engage the needle within the shield, the clip positioning member further including a retainer extending therefrom; and
a catheter disposed for slidable movement about the needle and a having a catheter introducer handle mounted to a proximal end of the needle such that the shield is disposed between the catheter and the catheter introducer handle, the catheter including a catheter hub having a flange circumferentially disposed thereabout, the retainer engaging the flange to releasably retain the catheter with shield.

16. The medical needle shield apparatus according to claim 15, wherein, in the distal position, the retainer releases the flange of the catheter hub from engagement with the shield.

17. The medical needle shield apparatus according to claim 15, wherein a hydrophobic filter is mounted with the shield adjacent a proximal end of the needle.

18. A medical needle shield apparatus comprising:
a shield being movable along a needle between a proximal position, whereby a distal end of the needle is exposed, and a distal position, whereby the shield encloses the distal end of the needle;
a clip disposed within the shield and defining a first aperture and a second aperture through which the needle passes, the first aperture and the second aperture defining binding surfaces configured to engage the needle; and
a clip positioning member disposed with the clip, the clip positioning member having a retention surface disposed at a first end thereof that is configured to engage the clip and a needle engaging surface, the needle engaging surface engaging the needle and the retention surface engaging the clip to maintain the clip in a biased state, the needle engaging surface being distally movable past the distal end of the needle such that the retention surface is releasable from engagement with the clip thereby disposing the clip in an unbiased state such that the binding surfaces engage the needle within the shield.

19. The medical needle shield apparatus according to claim 18, wherein medical needle device includes an introducer needle handle connected to an outer needle disposed for movement about the needle.

20. The medical needle shield apparatus according to claim 19, wherein the introducer needle handle is connected to a second shield for use with the outer needle, the second shield being slidably movable along the outer needle from a proximal position to a distal position where the second shield covers a distal end of the outer needle.

* * * * *